(12) United States Patent
Srinivasan et al.

(10) Patent No.: US 11,149,026 B2
(45) Date of Patent: Oct. 19, 2021

(54) SOLID STATE FORMS OF 5-CHLORO-6-[(2-IMINOPYRROLIDIN-1-YL) METHYL]PYRIMIDINE-2,4-(1H,3H)-DIONE HYDROCHLORIDE AND THEIR PROCESSES FOR THE PREPARATION THEREOF

(71) Applicant: MSN LABORATORIES PRIVATE LIMITED, R&D CENTER, Telangan (IN)

(72) Inventors: Thirumalai Rajan Srinivasan, Hyderabad (IN); Eswaraiah Sajja, Hyderabad (IN); Venkat Reddy Ghojala, Hyderabad (IN); Rajeshwar Reddy Sagyam, Hyderabad (IN); Srinivasulu Rangineni, Hyderabad (IN); Rajashekar Kommera, Hyderabad (IN); Markandeya Bekkam, Hyderabad (IN)

(73) Assignee: MSN LABORATORIES PRIVATE LIMITED, R&D CENTER, Telangana (IN)

( * ) Notice: Subject to any disclaimer, the term of this patent is extended or adjusted under 35 U.S.C. 154(b) by 32 days.

(21) Appl. No.: 16/645,472

(22) PCT Filed: Sep. 7, 2018

(86) PCT No.: PCT/IN2018/050583
§ 371 (c)(1),
(2) Date: Mar. 8, 2020

(87) PCT Pub. No.: WO2019/049174
PCT Pub. Date: Mar. 14, 2019

(65) Prior Publication Data
US 2020/0283413 A1    Sep. 10, 2020

(30) Foreign Application Priority Data

Sep. 7, 2017  (IN) .............................. 201741031748
Sep. 20, 2017 (IN) .............................. 201741033391
Apr. 2, 2018  (IN) .............................. 201841012427
Apr. 27, 2018 (IN) .............................. 201841015961

(51) Int. Cl.
*C07D 403/06*    (2006.01)

(52) U.S. Cl.
CPC ........ *C07D 403/06* (2013.01); *C07B 2200/13* (2013.01)

(58) Field of Classification Search
None
See application file for complete search history.

(56) References Cited

U.S. PATENT DOCUMENTS 9,527,833 B2 * 12/2016 Kazuno ................... A61P 35/00

* cited by examiner

*Primary Examiner* — Heidi Reese
(74) *Attorney, Agent, or Firm* — IP Pundit LLC

(57) ABSTRACT

The present invention relates to solid state forms of 5-chloro-6-[(2-iminopyrrolidin-1-yl)methyl]pyrimidine-2, 4-(1H,3H)-dione hydrochloride compound of formula-1a and their processes for the preparation thereof and an improved process for the preparation of 5-chloro-6-[(2-iminopyrrolidin-1-yl)methyl]pyrimidine-2,4-(1H,3H)-dione hydrochloride.

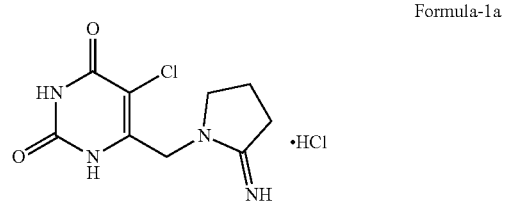

Formula-1a

The present inventors also provides an amorphous polymorph of the combination drug consisting of 2'-deoxy-5-(trifluoromethyl) uridine and 5-chloro-6-[(2-iminopyrrolidin-1-yl)methyl]pyrimidine-2,4-(1H,3H)-dione monohydrochloride and its process for the preparation.

13 Claims, 9 Drawing Sheets

SOLID STATE FORMS OF 5-CHLORO-6-[(2-IMINOPYRROLIDIN-1-YL) METHYL]PYRIMIDINE-2,4-(1H,3H)-DIONE HYDROCHLORIDE AND THEIR PROCESSES FOR THE PREPARATION THEREOF

RELATED APPLICATIONS

This application is a U.S. National Phase Entry of the International Patent Application Number PCT/IN2018/050583, filed on Sep. 7, 2018, which claims the benefit of priority to-Indian patent application numbers 201741031748 filed on Sep. 7, 2017; 201741033391 filed on Sep. 20, 2017; 201841012427 filed on Apr. 2, 2018 and 201841015961 filed on Apr. 27, 2018; the disclosures of all of which are incorporated herein by reference in their entirety.

FIELD OF THE INVENTION

The present invention relates to solid state forms of 5-chloro-6-[(2-iminopyrrolidin-1-yl)methyl]pyrimidine-2,4-(1H,3H)-dione hydrochloride compound of formula-1a and their processes for the preparation thereof.

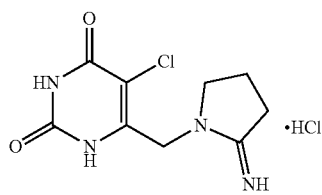

Formula-1a

The present invention also provides an improved process for the preparation of 5-chloro-6-[(2-iminopyrrolidin-1-yl)methyl]pyrimidine-2,4-(1H,3H)-dione hydrochloride.

The present inventors also provides an amorphous polymorph of the combination drug consisting of 2'-deoxy-5-(trifluoromethyl) uridine and 5-chloro-6-[(2-iminopyrrolidin-1-yl)methyl]pyrimidine-2,4-(1H,3H)-dione monohydrochloride and its process for the preparation.

BACKGROUND OF THE INVENTION 5-chloro-6-[(2-iminopyrrolidin-1-yl)methyl]pyrimidine-2,4-(1H,3H)-dione hydrochloride, commonly known as Tipiracil hydrochloride has an inhibitory action on human thymidine phosphorylase and an enhancing action on the antitumor effect of Trifluridine. Tipiracil prevents rapid metabolism of Trifluridine, increasing the bioavailability of Trifluridine. An antitumor agent "TAS-102" composed of a mixture of Trifluridine and Tipiracil hydrochloride with a molar ratio of 1:0.5 was approved by United States Food and Drug administration (USFDA) on Sep. 22, 2015 and by European medicines agency on Apr. 25, 2016 as a therapeutic agent indicated for the treatment of patients with metastatic colorectal cancer. The said combination product is marketed under the trade name Lonsurf®. TAS-102 is structurally shown as follows:

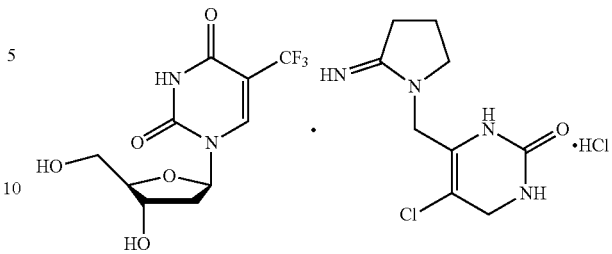

TAS-102

5-chloro-6-[(2-iminopyrrolidin-1-yl)methyl]pyrimidine-2,4-(1H,3H)-dione hydrochloride also known as 5-chloro-6-[(2-iminopyrrolidin-1-yl)methyl]pyrimidine-2,4-(1H,3H)-dione monohydrochloride.

Trifluridine is chemically known as 2'-deoxy-5-(trifluoromethyl) uridine and is first described in U.S. Pat. No. 3,201,387.

U.S. Pat. No. 5,744,475 patent discloses the combination of 2'-deoxy-5-(trifluoromethyl) uridine and 5-chloro-6-[(2-iminopyrrolidin-1-yl)methyl]pyrimidine-2,4-(1H,3H)-dione mono-hydrochloride in 1:0.5 molar ratio.

The present inventors also have developed an amorphous polymorph of the combination drug consisting of 2'-deoxy-5-(trifluoromethyl) uridine and 5-chloro-6-[(2-iminopyrrolidin-1-yl)methyl]pyrimidine-2,4-(1H,3H)-dione monohydrochloride and its process for the preparation.

U.S. Pat. No. 5,744,475A describes 5-chloro-6-[(2-iminopyrrolidin-1-yl)methyl]pyrimidine-2,4-(1H,3H)-dione hydrochloride, its analogs and process for their preparation.

U.S. Pat. No. 9,527,833B2 of Taiho pharmaceuticals has described three crystalline polymorphic forms of 5-chloro-6-[(2-iminopyrrolidin-1-yl)methyl]pyrimidine-2,4-(1H,3H)-dione hydrochloride namely crystalline form-I, II and III and processes for their preparation.

The present invention provides an improved process for the preparation of Tipiracil hydrochloride and its polymorphs.

The present invention also provides a process for the purification of Tipiracil and its intermediate compound.

BRIEF DESCRIPTION OF THE INVENTION

The first aspect of the present invention is to provide a novel crystalline polymorph of 5-chloro-6-[(2-iminopyrrolidin-1-yl)methyl]pyrimidine-2,4-(1H,3H)-dione hydrochloride compound of formula-1a.

The second aspect of the present invention is to provide a process for the preparation of novel crystalline polymorph of compound of formula-1a of the present invention.

The third aspect of the present invention is to provide pure amorphous form of compound of formula-1a.

The fourth aspect of the present invention is to provide a process for the preparation of pure amorphous form of compound of formula-1a.

The fifth aspect of the present invention is to provide amorphous solid dispersion comprising compound of formula-1a and at least one pharmaceutically acceptable excipient.

The sixth aspect of the present invention is to provide a process for the preparation of amorphous solid dispersion comprising compound of formula-1a and at least one pharmaceutically acceptable excipient.

The seventh aspect of the present invention is to provide an improved process for the preparation of 5-chloro-6-[(2-iminopyrrolidin-1-yl)methyl]pyrimidine-2,4-(1H,3H)-dione hydrochloride compound of formula-1a.

The eighth aspect of the present invention is to provide a process for the purification of 5-chloro-6-(chloromethyl) pyrimidine-2,4(1H,3H)-dione compound of formula-3a, which is an useful intermediate for the preparation of compound of formula-1a.

The ninth aspect of the present invention is to provide a process for the purification of 5-chloro-6-[(2-iminopyrrolidin-1-yl)methyl]pyrimidine-2,4-(1H,3H)-dione compound of formula-1.

The tenth aspect of the present invention is to provide a process for the preparation of crystalline form-I of 5-chloro-6-[(2-iminopyrrolidin-1-yl)methyl]pyrimidine-2,4-(1H, 3H)-dione hydrochloride compound of formula-1a.

The eleventh aspect of the present invention is to provide a process for the preparation of crystalline form-II of compound of formula-1a.

The twelfth aspect of the present invention is to provide alternate process for the preparation of crystalline form-I of compound of formula-1a.

The thirteenth aspect of the present invention is to provide a novel crystalline polymorph of 5-chloro-6-[(2-iminopyrrolidin-1-yl)methyl]pyrimidine-2,4-(1H,3H)-dione hydrochloride compound of formula-1a.

The fourteenth aspect of the present invention is to provide a process for the preparation of novel crystalline polymorph of compound of formula-1a of the present invention.

The fifteenth aspect of the present invention is to provide the amorphous polymorph of the combination drug consisting of 2'-deoxy-5-(trifluoromethyl) uridine and 5-chloro-6-[(2-iminopyrrolidin-1-yl)methyl] pyrimidine-2,4-(1H,3H)-dione monohydrochloride.

BRIEF DESCRIPTION OF THE DRAWINGS

FIG. 2: Illustrates the PXRD pattern of pure amorphous form of compound of formula-1a.

DETAILED DESCRIPTION OF THE INVENTION

Figure 1:
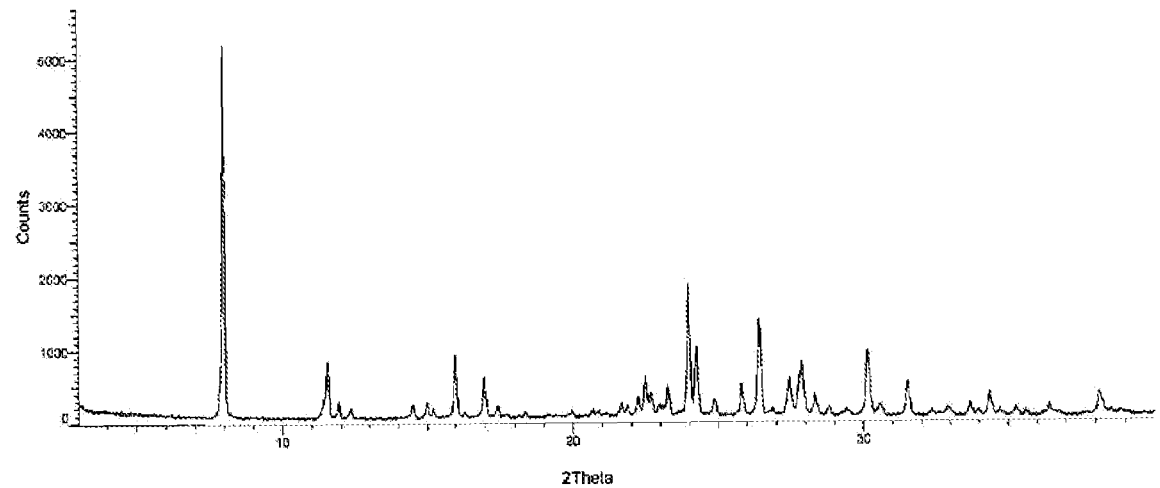
FIG. 1: Illustrates the PXRD pattern of novel crystalline polymorph of compound of formula-1a of the present invention.

The "suitable solvent" used in the present invention can be selected from but not limited to "hydrocarbon solvents" such as n-pentane, n-hexane, n-heptane, cyclohexane, petroleum ether, benzene, toluene, xylene and the like; "ether solvents" such as dimethyl ether, diethyl ether, diisopropyl ether, methyl tert-butyl ether, 1,2-dimethoxyethane, tetrahydrofuran, 1,4-dioxane and the like; "ester solvents" such as methyl acetate, ethyl acetate, n-propyl acetate, isopropyl acetate, n-butyl acetate, isobutyl acetate, tert-butyl acetate and the like; "polar-aprotic solvents" such as dimethylacetamide, dimethylformamide, dimethylsulfoxide, N-methylpyrrolidone (NMP) and the like; "chloro solvents" such as dichloromethane, dichloroethane, chloroform, carbon tetrachloride and the like; "ketone solvents" such as acetone, methyl ethyl ketone, methyl isobutyl ketone and the like; "nitrile solvents" such as acetonitrile, propionitrile, isobutyronitrile and the like; "alcohol solvents" such as methanol, ethanol, n-propanol, iso-propanol, n-butanol, iso-butanol, 2-butanol, tert-butanol, ethane-1,2-diol, propane-1,2-diol and the like; "polar solvents" such as water; formic acid, acetic acid, hydrochloric acid, sulfuric acid and the like or mixture of any of the afore mentioned solvents.

The "suitable base" used in the present invention can be selected from but not limited to "inorganic bases" selected from "alkali metal carbonates" such as sodium carbonate, potassium carbonate, lithium carbonate, cesium carbonate and the like; "alkali metal bicarbonates" such as sodium bicarbonate, potassium bicarbonate, lithium bicarbonate, cesium bicarbonate and the like; "alkali metal hydroxides" such as sodium hydroxide, potassium hydroxide, lithium hydroxide, cesium hydroxide and the like; "alkali metal alkoxides" such as sodium methoxide, sodiumethoxide, potassium methoxide, potassiumethoxide, lithium methoxide, lithiumethoxide, sodium tert.butoxide, potassium tert.butoxide, lithium tert.butoxide and the like; "alkali metal hydrides" such as sodium hydride, potassium hydride, lithium hydride and the like; "alkali metal amides" such as sodium amide, potassium amide, lithium amide and the like; alkali metal and alkali earth metal salts of acetic acid such as sodium acetate, potassium acetate, magnesium acetate, calcium acetate and the like; ammonia; "organic bases" like dimethylamine, diethylamine, diisopropylamine, diisopropylethylamine (DIPEA), diisobutylamine, triethylamine, triisopropyl amine, tributylamine, tert.butyl amine, pyridine, piperidine, 4-dimethylaminopyridine (DMAP), quinoline, imidazole, N-methylimidazole, 1,8-diazabicyclo[5.4.0]undec-7-ene (DBU), 1,5-diazabicyclo[4.3.0]non-5-ene (DBN), dimethylaniline, N-methylmorpholine (NMM), 1,4-diazabicyclo[2.2.2]octane (DABCO), 2,6-lutidine and the like; "organolithium bases" such as methyl lithium, n-butyl lithium, lithium diisopropylamide (LDA) and the like; "organosilicon bases" such as lithium hexamethyldisilazide (LiHMDS), sodium hexamethyldisilazide (NaHMDS), potassium hexamethyldisilazide (KHMDS) and the like or their mixtures.

As used herein the term "pharmaceutically acceptable salts" or "salts" in the present invention refers to acid addition salts selected from inorganic acids such as hydrochloric acid, hydrobromic acid, sulfuric acid, nitric acid, phosphoric acid; organic acids such as acetic acid, maleic acid, malic acid, oxalic acid, trifluoroacetic acid, methane sulfonic acid, p-toluene sulfonic acid; chiral acids such as S-(+) mandelic acid, R-(−) mandelic acid, L-(+)tartaric acid, D-(−)tartaric acid, L-malic acid, D-malic acid, D-maleic acid, (−)-naproxen, (+)-naproxen, (IR)-(−)-camphor sulfonic acid, (IS)-(+)-camphor sulfonic acid (IR)-(+)-bromo-camphor-10-sulfonic acid, (IS)-(−)-bromocamphor-10-sulfonic acid, (−)-Dibenzoyl-L-tartaric acid, (−)-Dibenzoyl-L-tartaric acid monohydrate, (+)-Dibenzoyl-D-tartaric acid, (+)-Dibenzoyl-D-tartaric acid monohydrate, (+)-diparatolyl-D-tataric acid, (−)-dipara-tolyl-L-tataric acid, L(−)-pyroglutamic acid, L(+)-pyroglutamic acid, (−)-lactic acid, L-lysine, D-lysine etc., and like.

The suitable "Lewis acid" is selected aluminum chloride, aluminum bromide, boron trifluoride, boron tribromide, tin tetrachloride, tin tetrabromide, stannous chloride ($SnCl_2$), ferric chloride ($FeCl_3$), zinc chloride ($ZnCl_2$), titanium tetrachloride ($TiCl_4$) or mixtures or hydrates thereof.

The first aspect of the present invention provides a novel crystalline polymorph of 5-chloro-6-[(2-iminopyrrolidin-1-yl)methyl]pyrimidine-2,4-(1H,3H)-dione hydrochloride compound of formula-1a. The said novel crystalline polymorph is characterized by its PXRD pattern as illustrated in FIG. 1.

Further embodiment of the present invention provides the above novel crystalline form is having dimethyl sulfoxide content in the range of about 18 to about 25% w/w and also the said crystalline form is defined as dimethyl sulfoxide solvate. The structure of the said compound is shown as follows:

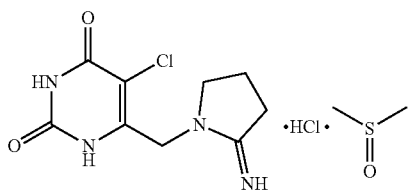

Figure 6:
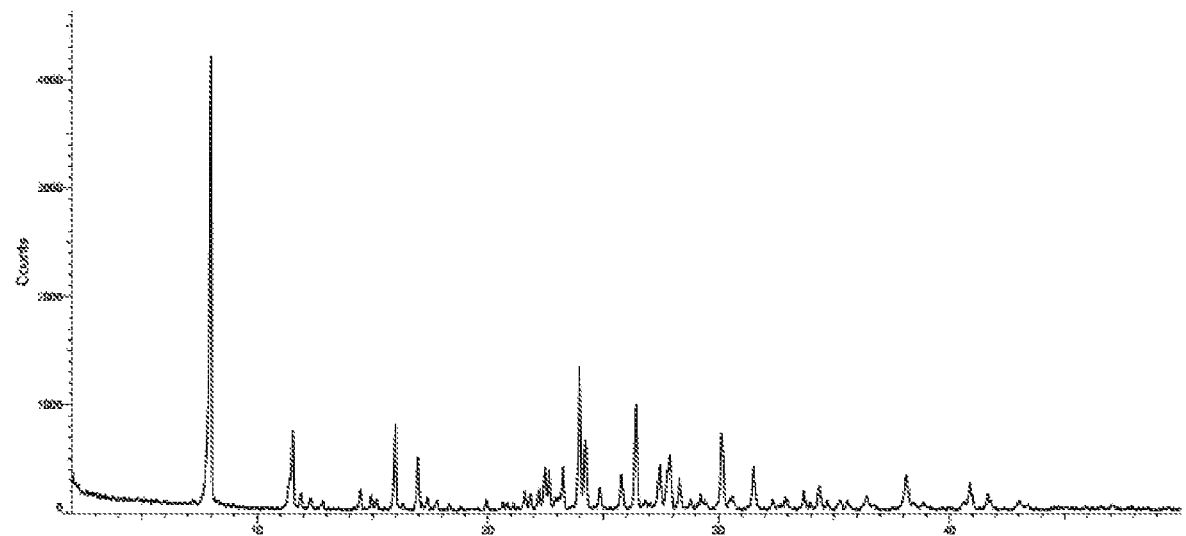
FIG. 6: Illustrates the PXRD pattern of 5-chloro-6-[(2-iminopyrrolidin-1-yl)methyl]pyrimidine-2,4-(1H,3H)-dione hydrochloride dimethyl sulfoxide solvate obtained according to example-23.

Further embodiment of the present invention provides dimethyl sulfoxide solvate of compound of formula-1a is characterized by its powder X-ray diffraction pattern having peaks at 7.9°, 15.9° and 16.9° (±0.2° 2θ) and further the peaks at about 11.5°, 14.4°, 17.0°, 23.2°, 23.9°, 25.8° and 26.4° 2θ (±0.2° 2θ). The crystalline form (herein after referred as form-M) is characterized by its PXRD pattern as illustrated in FIG. 1 and FIG. 6.

Figure 7:
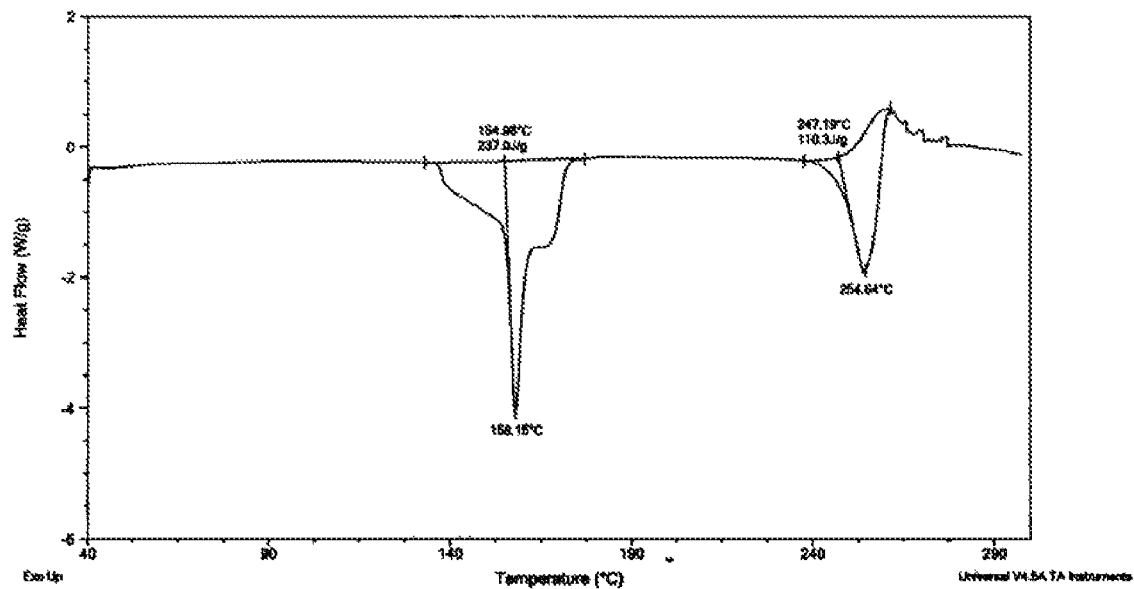
FIG. 7: Illustrates the DSC thermogram of 5-chloro-6-[(2-iminopyrrolidin-1-yl)methyl]pyrimidine-2,4-(1H,3H)-dione hydrochloride dimethyl sulfoxide solvate obtained according to example-23.

Further embodiment of the present invention provides dimethyl sulfoxide solvate of compound of formula-1a is characterized by its DSC thermogram which is illustrated in figure-7.

The second aspect of the present invention provides a process for the preparation of novel crystalline polymorph of compound of formula-1a having PXRD pattern as shown in FIG. 1, comprising of;
a) Providing a solution of compound of formula-1a in dimethylsulfoxide optionally in mixture with a first solvent,
b) optionally filtering the reaction mixture,
c) combining the solution with a suitable second solvent at a suitable temperature to provide novel crystalline polymorph of compound of formula-1a.

Wherein, in one embodiment of above step-a) providing the solution of compound of formula-1a can be done by combining the compound of formula-1a with dimethylsulfoxide optionally in mixture with a first solvent and optionally heating the reaction mixture to a suitable temperature ranges from 35° C. to 150° C.

In other embodiment of step-a) of the present invention, dimethylsulfoxide can be added to a pre-heated mixture of compound of formula-1a and first solvent.

In another embodiment, first solvent can be added to a pre-heated mixture of compound of formula-1a and dimethylsulfoxide.

The suitable first solvent can be selected from but not limited to polar solvents such as water, polar-aprotic solvents, alcohol solvents, ether solvents or mixtures thereof.

In step-c) the suitable second solvent can be selected from but not limited to ketone solvents, ester solvents, hydrocarbon solvents, chloro solvents, nitrile solvents or mixtures thereof; and the suitable temperature ranges from −20° C. to 100° C.

Preferred embodiment of the present invention provides a process for the preparation of novel crystalline polymorph of compound of formula-1a having PXRD pattern as shown in FIG. 1, comprising of;
a) providing a solution of compound of formula-1a in dimethylsulfoxide,
b) filtering the mixture obtained in step-a),
c) combining the solution with isobutyl acetate at about 25 to 35° C. to provide novel crystalline polymorph of compound of formula-1a.

Further aspect of the present invention provides a process for the preparation of crystalline 5-chloro-6-[(2-iminopyrrolidin-1-yl)methyl]pyrimidine-2,4-(1H,3H)-dione hydrochloride dimethyl sulfoxide solvate, comprising:
a) providing the solution of the compound of formula-1a in dimethyl sulfoxide,
b) combining the solution with a suitable second solvent at a suitable temperature to provide crystalline 5-chloro-6-[(2-iminopyrrolidin-1-yl)methyl]pyrimidine-2,4-(1H, 3H)-dione hydrochloride dimethyl sulfoxide solvate.

Wherein, in step-a) providing the solution of compound of formula-1a can be done by combining the compound of formula-1 with dimethylsulfoxide optionally in mixture with a first solvent, by adding a suitable hydrochloric acid source and optionally heating the reaction mixture to a suitable temperature ranges from 35° C. to 100° C. and the suitable first solvent can be selected from but not limited to polar solvents such as water, polar-aprotic solvents, alcohol solvents, ether solvents or mixtures thereof; the suitable HCl source can be selected from but not limited to conc.HCl, dry HCl, HCl gas, aq.HCl, methanol-HCl, ethanol-HCl, isopropyl alcohol-HCl, ethyl acetate-HCl, 1,4-dioxane-HCl and the like;

In step-b) the suitable second solvent can be selected from but not limited to ketone solvents, ester solvents, hydrocarbon solvents, chloro solvents, nitrile solvents or mixtures thereof; and the suitable temperature ranges from −20° C. to 100° C.; preferably 0° C. to 30° C.

Preferred embodiment of the present invention provides a process for the preparation of crystalline form of 5-chloro-6-[(2-iminopyrrolidin-1-yl)methyl]pyrimidine-2,4-(1H,3H)-dione hydrochloride dimethyl sulfoxide solvate

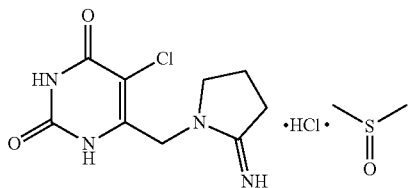

having PXRD pattern as shown in FIG. 1 or FIG. 6, comprising:
a) combining the compound of formula-1, dimethylsulfoxide and aqueous hydrochloric acid,
b) heating the mixture obtained in step-a) to 45-60° C.,
c) combining the solution with isobutyl acetate to provide crystalline dimethyl sulfoxide solvate of compound of formula-1a.

Figure 2:
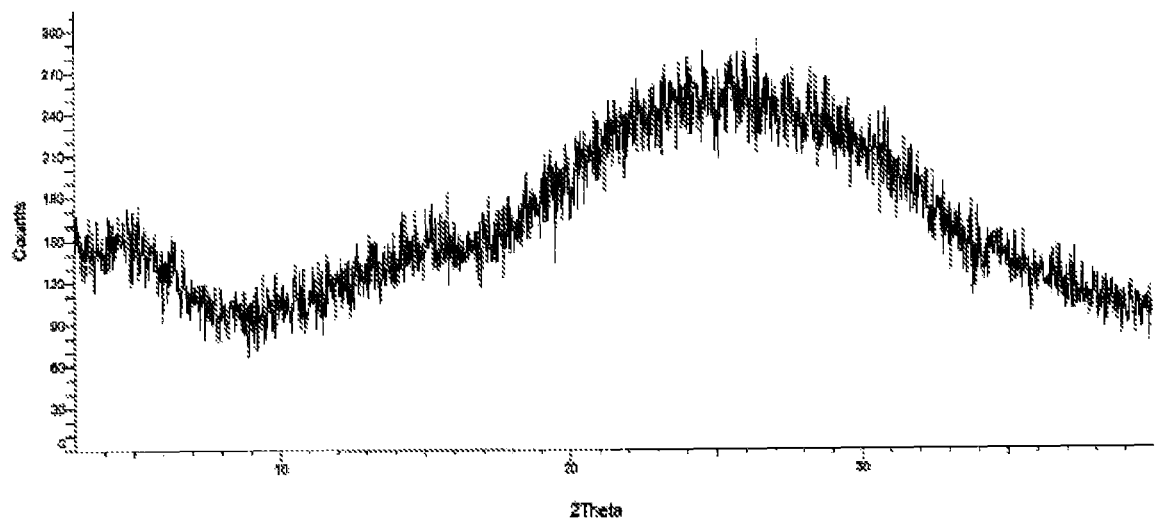

The third aspect of the present invention provides pure amorphous form of compound of formula-1a. The said pure amorphous form is characterized by its PXRD pattern as illustrated in FIG. 2.

"Pure amorphous" as used herein refers having polymorphic purity greater than 90%. It can provide the amorphous form of compound of formula-1a having less than 10% of crystalline compound of formula-1a, preferably less than 5%. It can also provide amorphous form of compound of formula-1a having less than 1% of crystalline form of compound of formula-1a, for example with no detectable amount of any crystalline forms.

The fourth aspect of the present invention provides a process for the preparation of pure amorphous form of compound of formula-1a, comprising of;
a) providing a solution of compound of formula-1a in a suitable solvent,
b) optionally filtering the reaction mixture,
c) removing the solvent from the reaction mixture to provide pure amorphous form of compound of formula-1a.

Wherein, in step-a) the suitable solvent can be selected from but not limited to hydrocarbon solvents, alcohol solvents, polar-aprotic solvents, polar solvents, chloro solvents, ether solvents, ester solvents, nitrile solvents, ketone solvents or mixtures thereof.

In the above process, providing a solution of compound of formula-1a in a suitable solvent or mixture of solvents can be done by combining the compound of formula-1a with any of the above described solvents or their mixtures and optionally heating the reaction mixture to a suitable temperature ranges from 35° C. to 150° C. (or)

can be done by combining the compound of formula-1 with any of the above described solvents or their mixtures, by adding a suitable hydrochloric acid source and optionally heating the reaction mixture to a suitable temperature ranges from 35° C. to 100° C.; the suitable HCl source can be selected from but not limited to conc.HCl, dry HCl, HCl gas, aq.HCl, methanol-HCl, ethanol-HCl, isopropyl alcohol-HCl, ethyl acetate-HCl, 1,4-dioxane-HCl and the like;

In another embodiment, the solution of step-a) can also be obtained directly from the synthetic procedure in which the compound of formula-1a was prepared.

Preferred embodiment of the present invention provides a process for the preparation of pure amorphous form of compound of formula-1a, comprising of;
a) dissolving the compound of formula-1a in the mixture of water and acetone,
b) spray drying the solution obtained in step-a) to provide pure amorphous form of compound of formula-1a.

The pure amorphous form of compound of formula-1a of the present invention is useful for the preparation of various pharmaceutical formulations.

An embodiment of the present invention provides use of pure amorphous form of compound of formula-1a for the preparation of various pharmaceutical formulations.

The other embodiment of the present invention provides pharmaceutical composition comprising pure amorphous form of compound of formula-1a and at least one pharmaceutically acceptable excipient.

The fifth aspect of the present invention provides amorphous solid dispersion comprising compound of formula-1a and at least one pharmaceutically acceptable excipient.

As used herein, the term "solid dispersion" means any solid composition having at least two components. In certain embodiments, a solid dispersion as disclosed herein includes an active ingredient (compound of formula-1a) dispersed among at least one other component, for example an excipient.

In the present invention, the excipient can be selected from but not limited to polyvinylpyrrolidone (povidone or PVP; PVP of different grades like K-15, K-30, K-60, K-90 and K-120 may be used), polyvinylpolypyrrolidone, polysorbate, cross linked polyvinyl pyrrolidone (crospovidone), Eudragit, polyethylene glycol (macrogol or PEG), polyvinyl alcohol, polyvinyl chloride, polyvinyl acetate, propylene glycol, cellulose, cellulose acetate phthalate (CAP), methyl cellulose, carboxymethyl cellulose (CMC, its sodium and calcium salts), carboxymethylethyl cellulose (CMEC), ethyl cellulose, hydroxymethyl cellulose, ethyl hydroxyethyl cellulose, hydroxyethylcellulose, hydroxypropyl cellulose (HPC), hydroxypropyl cellulose acetate succinate, hydroxypropyl methyl cellulose (hypromellose or HPMC), hydroxypropyl methylcellulose acetate succinate (HPMC-AS), hydroxyethyl methyl cellulose succinate (HEMCS), hydroxypropyl cellulose acetate succinate (HPCAS), hydroxypropyl methylcellulose phthalate (HPMC-P), hydroxypropyl methylcellulose acetate phthalate, microcrystalline cellulose (MCC), cross linked sodium carboxymethyl cellulose (croscarmellose sodium), cross linked calcium carboxymethyl cellulose, magnesium stearate, aluminium stearate, calcium stearate, magnesium carbonate, talc, iron oxide (red, yellow, black), stearic acid, dextrates, dextrin, dextrose, sucrose, glucose, xylitol, lactitol, sorbitol, mannitol, maltitol, maltose, raffinose, fructose, maltodextrin, anhydrous lactose, lactose monohydrate, starches such as maize starch or corn starch, sodium starch glycolate, sodium carboxymethyl starch, pregelatinized starch, gelatin, sodium dodecyl sulfate, edetate disodium, sodium phosphate, sodium lauryl sulfate, triacetin, sucralose, calcium phosphate, polydextrose, α-, β-, γ-cyclodextrins, sulfobutylether beta-cyclodextrin, sodium stearyl fumarate, fumaric acid, alginic acid, sodium alginate, propylene glycol alginate, citric acid, succinic acid, carbomer, docusate sodium, glyceryl behenate, glyceryl stearate, meglumine, arginine, polyethylene oxide, polyvinyl acetate phthalates and the like.

The solid state forms of compound of formula-1a of the present invention are having purity of greater than 98%, preferably greater than 99% by HPLC and is useful for the preparation of various pharmaceutical compositions formulated in a manner suitable for the route of administration to be used where at least a portion of compound of formula-1a is present in the composition in particular polymorphic form mentioned. Such pharmaceutical compositions may comprise compound of formula-1a present in the composition in a range of between 0.005% and 100% (wt/wt), with the balance of the pharmaceutical composition comprising additional substances such as excipients, diluents, lubricants, binders, wetting agents, disintegrating agents, glidants, sweetening agents, flavoring agents, emulsifying agents, solubilizing agents, pH buffering agents, perfuming agents, surface stabilizing agents, suspending agents and other conventional pharmaceutically inactive agents.

The sixth aspect of the present invention provides a process for the preparation of amorphous solid dispersion comprising compound of formula-1a and at least one pharmaceutically acceptable excipient. The said process comprising of;
a) Providing a solution of compound of formula-1a and at least one excipient in a suitable solvent,
b) optionally filtering the reaction mixture,
c) removing the solvent from the reaction mixture to provide amorphous solid dispersion comprising compound of formula-1a and corresponding excipient.

Wherein, in step-a) the excipient is same as defined above; and the suitable solvent is same as defined in step-a) of the forth aspect of the present invention.

In the above process, providing a solution of compound of formula-1a and at least one excipient in a suitable solvent or mixture of solvents can be done by combining the compound of formula-1a and excipient with any of the above described solvents and optionally heating the reaction mixture to a suitable temperature ranges from 35° C. to 150° C.

The solution provided in step-a) of the fourth aspect or step-a) of the sixth aspect of the present invention may optionally be treated with charcoal or any other suitable material to remove color and/or to clarify the solution and the solution may optionally be filtered to make it particle free.

In the present invention, filtering the reaction mixture/solution to make it particle free can be carried out by passing through paper, cloth, glass fiber or other membrane material or a bed of a clarifying agent such as Celite® or hyflow. Depending upon the equipment used and the concentration and temperature of the solution, the filtration apparatus may need to be preheated to avoid premature crystallization.

In the above described processes, the suitable techniques which may be used for the removal of solvent from the reaction mixture includes but not limited to evaporation optionally under reduced pressure, flash evaporation, vacuum drying, concentrating the reaction mixture, atmospheric distillation, distillation under reduced pressure, distillation by using a rotational distillation device such as a Buchi Rotavapor, agitated thin film drying (ATFD), melt extrusion, spray drying, freeze drying (lyophilization), spray-freeze drying, adding a suitable anti-solvent to the reaction mixture followed by filtration of the precipitated solid, cooling the clear solution to lower temperatures to precipitate the solid followed by filtration of the reaction mixture or by any other suitable techniques known in the art.

In one embodiment, the suitable anti-solvent can be selected from but not limited to ketone solvents, ester solvents, hydrocarbon solvents, chloro solvents, nitrile solvents or mixtures thereof.

The solvent may be removed optionally under reduced pressures, at temperatures less than about 200° C., less than about 150° C., less than about 100° C., less than about 60° C., less than about 40° C., less than about 20° C., less than about 0° C., less than about −20° C., less than about −40° C. or less than about −60° C.

In the present invention, the ratio of the amount by weight of compound of formula-1a within the solid dispersion to the amount by weight of the excipient therein ranges from but not limited to about 1:0.05 to about 1:5.

In the above processes, the compound of formula-1a which is used as input for the preparation of solid state forms of compound of formula-1a of the present invention can be prepared by any of the processes known in the art.

The seventh aspect of the present invention provides a process for the preparation of 5-chloro-6-[(2-iminopyrrolidin-1-yl)methyl]pyrimidine-2,4-(1H,3H)-dione hydrochloride compound of formula-1a, comprising:
a) chlorination of 6-(halomethyl)pyrimidine-2,4-(1H,3H)-dione compound of general formula-2

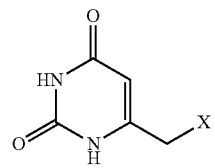

Formula-2 wherein, 'X' represents halogen such as F, Cl, Br & I;
by treating it with a suitable chlorinating agent optionally in presence of a suitable solvent to provide 5-chloro-6-(halomethyl)pyrimidine-2,4-(1H,3H)-dione compound of general formula-3,

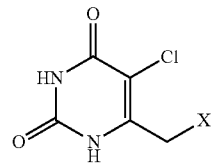

Formula-3 wherein, 'X' is as defined above;
b) reacting the compound of general formula-3 with pyrrolidin-2-imine compound of formula-4 or its salt

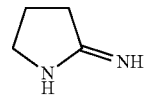

Formula-4 in a suitable solvent optionally in presence of a suitable base to provide 5-chloro-6-[(2-iminopyrrolidin-1-yl)methyl]pyrimidine-2,4-(1H,3H)-dione compound of formula-1, Formula-1

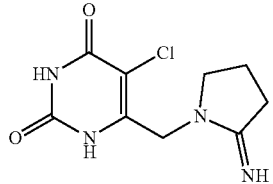

c) treating the compound of formula-1 with a suitable HCl source optionally in presence of a suitable solvent to provide corresponding hydrochloride salt compound of formula-1a.

Wherein, in step-a) the suitable chlorinating agent can be selected from but not limited to N-chlorosuccinimide (NCS), $Cl_2$, sulfuryl chloride, thionyl chloride, oxalyl chloride, $PCl_5$, $PCl_3$, $POCl_3$, cyanuric chloride, trichloroisocyanuric acid or combination thereof;

In step-b) the suitable base can be selected from but not limited to inorganic bases, organic bases, organolithium bases, organosilicon bases and the like or mixtures thereof;

In step-a) & step-b) the suitable solvent can be selected from but not limited to hydrocarbon solvents, ether solvents, ester solvents, polar-aprotic solvents, chloro solvents, ketone solvents, nitrile solvents, alcohol solvents, polar solvents, formic acid, acetic acid, hydrochloric acid, sulfuric acid and the like or mixtures thereof;

In step-c) the suitable HCl source can be selected from but not limited to conc.HCl, dry HCl, HCl gas, aq.HCl, methanol-HCl, ethanol-HCl, isopropyl alcohol-HCl, ethyl acetate-HCl, 1,4-dioxane-HCl and the like; and the suitable solvent can be selected from but not limited to hydrocarbon solvents, ether solvents, ester solvents, polar-aprotic solvents, chloro solvents, ketone solvents, nitrile solvents, alcohol solvents, polar solvents and the like or mixtures thereof.

Preferred embodiment of the present invention provides a process for the preparation of 5-chloro-6-[(2-iminopyrrolidin-1-yl)methyl]pyrimidine-2,4-(1H,3H)-dione hydrochloride compound of formula-1a, comprising of;

a) Chlorination of 6-(chloromethyl)pyrimidine-2,4(1H,3H)-dione compound of formula-2a Formula-2a

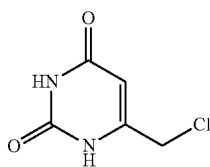

by treating it with sulfuryl chloride in acetic acid to provide 5-chloro-6-(chloromethyl)pyrimidine-2,4(1H,3H)-dione compound of formula-3a Formula-3a

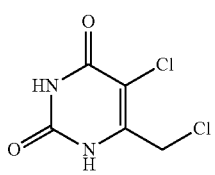

b) reacting the compound of formula-3a with pyrrolidin-2-imine hydrochloride

Formula-4a

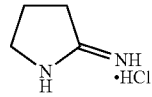

in methanol in presence of DBU provide 5-chloro-6-[(2-iminopyrrolidin-1-yl)methyl]pyrimidine-2,4-(1H,3H)-dione compound of formula-1, Formula-1

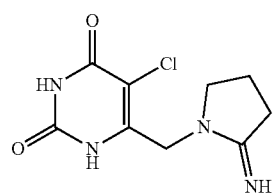

c) treating the compound of formula-1 with HCl in water to provide the compound of formula-1a.

In step-a) of the above described process, after completion of the chlorination step, about 5% of the unreacted starting material compound of formula-2a (when X═Cl) has been observed as an impurity in the compound of formula-3a (when X═Cl).

Hence, an efficient purification process is highly required to remove the said impurity from compound of formula-3a, which otherwise leads to the formation of many impurities in the subsequent process steps that greatly effects the quality and cost of the product.

The present inventors after earnest efforts have developed the below process for the purification of compound of formula-3a which reduces the starting material impurity to significantly lower levels.

The eighth aspect of the present invention provides a process for the purification of 5-chloro-6-(chloromethyl)pyrimidine-2,4(1H,3H)-dione compound of formula-3a, comprising of;

a) providing a solution of compound of formula-3a in a suitable solvent, b) combining the solution with a suitable anti-solvent at a suitable temperature and optionally cooling the reaction mixture to provide pure compound of formula-3a.

Wherein, in step-a) the suitable solvent can be selected from but not limited to polar-aprotic solvents or mixture of polar-aprotic solvents;

In step-b) the suitable anti-solvent can be selected from but not limited to hydrocarbon solvents, ether solvents, ester solvents, chloro solvents, ketone solvents, nitrile solvents, alcohol solvents, polar solvents and the like or mixtures thereof; and the suitable temperature ranges from 25° C. to reflux temperature of the solvent used.

In step-b) the reaction mixture can be optionally cooled to a lower temperature ranges from −70° C. to 20° C. to reduce the yield loss in the purification process.

An embodiment of the present invention provides a process for the purification of 5-chloro-6-(chloromethyl) pyrimidine-2,4(1H,3H)-dione compound of formula-3a, comprising of;

a) adding a suitable solvent to compound of formula-3a,
b) heating the reaction mixture to a suitable temperature,
c) optionally cooling the reaction mixture,
d) combining the reaction mixture with a suitable anti-solvent at a suitable temperature and optionally cooling the reaction mixture to provide pure compound of formula-3a.

Wherein, in step-a) the suitable solvent is same as defined in step-a) of the second aspect of the present invention;

In step-b) the suitable temperature ranges from 30° C. to reflux temperature of the solvent used;

In step-c) the reaction mixture can be optionally cooled to a suitable temperature ranges from 25-30° C.;

In step-d) the suitable anti-solvent and the suitable temperature are same as defined in step-b) of the second aspect of the present invention;

In step-d) the reaction mixture can be optionally cooled to a lower temperature ranges from −70° C. to 20° C.

Preferred embodiment of the present invention provides a process for the purification of 5-chloro-6-(chloromethyl) pyrimidine-2,4(1H,3H)-dione compound of formula-3a, comprising of;
a) dissolving the compound of formula-3a in dimethyl formamide,
b) combining the solution with water to provide pure compound of formula-3a.

After purifying the compound of formula-3a by the above described process, the starting material impurity level in compound of formula-3a is reduced to a significantly low level of about 0.5%.

Hence, the above purification process is highly advantageous and provides pure intermediate compound of formula-3a, which in turn leads to compound of formula-1a with enhanced purity.

After performing the above purification process, the unmoved starting material impurity of formula-2a is carried over in the subsequent coupling step and lead to the formation of following compounds as impurities in compound of formula-1.

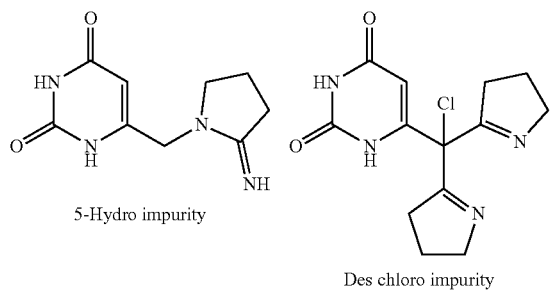

5-Hydro impurity

Des chloro impurity

Further, the starting material compound of formula-2a and intermediate compound of formula-3a are genotoxic compounds, which should be controlled in the compound of formula-1a to significantly lower levels to meet the regulatory requirements.

Hence, there is a significant need to develop a process for the purification of compound of formula-1 to remove the above mentioned impurities.

The present inventors after significant number of experiments, surprisingly found the below purification process which efficiently washed out the above said impurities and provided the compound of formula-1 with more than 99% purity, which is highly advantageous.

The highly pure compound of formula-1 obtained by the above purification process in turn leads to the compound of formula-1a with much enhanced purity.

The ninth aspect of the present invention provides a process for the purification of 5-chloro-6-[(2-iminopyrrolidin-1-yl)methyl]pyrimidine-2,4-(1H,3H)-dione compound of formula-1, comprising of;
a) treating the compound of formula-1 with a suitable acid in a suitable solvent,
b) optionally isolating the corresponding acid-addition salt from the reaction mixture,
c) treating the reaction mixture of step-a) or the compound of step-b) with a suitable base in a suitable solvent to provide pure compound of formula-1.

Wherein, in step-a) the suitable acid can be selected from but not limited to "inorganic acids" such as hydrochloric acid, hydrobromic acid, sulfuric acid, nitric acid and phosphoric acid; and "organic acids" such as formic acid, acetic acid, propionic acid, butyric acid, valeric acid, caproic acid, trifluoroacetic acid, trifluoromethanesulfonic acid, oxalic acid, malonic acid, maleic acid, fumaric acid, malic acid, succinic acid, citric acid, aspartic acid, tartaric acid, mandelic acid, benzoic acid, salicylic acid, substituted/unsubstituted alkyl/aryl sulfonic acids such as methanesulfonic acid, ethanesulfonic acid, propanesulfonic acid, benzenesulfonic acid, p-toluenesulfonic acid, naphthalenesulfonic acid and the like;

In step-c) the suitable base can be selected from inorganic bases, organic bases or mixtures thereof;

In step-a) and step-c) the suitable solvent can be independently selected from hydrocarbon solvents, ether solvents, ester solvents, polar-aprotic solvents, chloro solvents, ketone solvents, nitrile solvents, alcohol solvents, polar solvents or mixtures thereof.

Preferred embodiment of the present invention provides a process for the purification of 5-chloro-6-[(2-iminopyrrolidin-1-yl)methyl]pyrimidine-2,4-(1H,3H)-dione compound of formula-1, comprising;
a) treating the compound of formula-1 with dilute/aqueous hydrochloric acid in water,
b) treating the mixture obtained in step-a) with triethylamine to provide pure compound of formula-1.

The present invention is schematically represented as follows:

Scheme-I

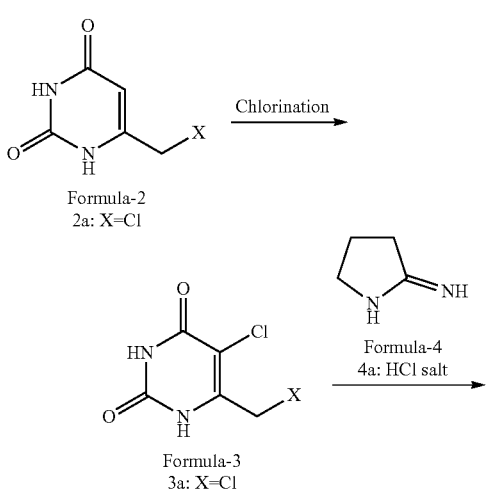

Formula-2
2a: X=Cl

Formula-4
4a: HCl salt

Formula-3
3a: X=Cl

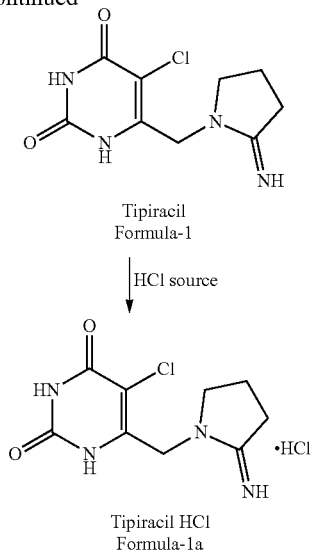

Wherein, 'X' represents halogens such as F, Cl, Br & I.

The tenth aspect of the present invention provides a process for the preparation of crystalline form-I of 5-chloro-6-[(2-iminopyrrolidin-1-yl)methyl]pyrimidine-2,4-(1H,3H)-dione hydrochloride compound of formula-1a, comprising of;
a) adding hydrochloric acid to a mixture of 5-chloro-6-[(2-iminopyrrolidin-1-yl)methyl]pyrimidine-2,4-(1H,3H)-dione compound of formula-1 and a suitable solvent at a suitable temperature,
b) optionally filtering the reaction mixture,
c) adding hydrochloric acid to the reaction mixture at a suitable temperature,
d) cooling the reaction mixture to a suitable temperature to precipitate crystalline form-I of compound of formula-1a.

Wherein, in step-a) the suitable solvent can be selected from hydrocarbon solvents, ether solvents, ester solvents, polar-aprotic solvents, chloro solvents, ketone solvents, nitrile solvents, alcohol solvents, polar solvents or mixtures thereof.

In step-a) & step-c) the suitable temperature is 25-30° C.;
In step-d) the suitable temperature ranges from −10° C. to 10° C.

Preferred embodiment of the present invention provides a process for the preparation of crystalline form-I of 5-chloro-6-[(2-iminopyrrolidin-1-yl)methyl]pyrimidine-2,4-(1H,3H)-dione hydrochloride compound of formula-1a, comprising:
a) adding diluted or aqueous hydrochloric acid solution to a mixture of 5-chloro-6-[(2-iminopyrrolidin-1-yl)methyl]pyrimidine-2,4-(1H,3H)-dione compound of formula-1 and water,
b) filtering the reaction mixture,
c) adding hydrochloric acid to the reaction mixture at a suitable temperature,
d) cooling the reaction mixture to a suitable temperature to precipitate crystalline form-I of compound of formula-1a.

The eleventh aspect of the present invention provides a process for the preparation of crystalline form-II of compound of formula-1a, comprising of;
a) adding hydrochloric acid to a mixture of compound of formula-1 and a suitable solvent at a suitable temperature,
b) optionally filtering the reaction mixture,
c) cooling the reaction mixture to a suitable temperature,
d) slowly adding hydrochloric acid to the reaction mixture,
e) further cooling the reaction mixture to a suitable temperature,
f) adding hydrochloric acid to the reaction mixture to precipitate crystalline form-II of compound of formula-1a.

Wherein, in step-a) the suitable solvent can be selected from hydrocarbon solvents, ether solvents, ester solvents, polar-aprotic solvents, chloro solvents, ketone solvents, nitrile solvents, alcohol solvents, polar solvents or mixtures thereof; and the suitable temperature is 25-30° C.;
In step-c) the suitable temperature ranges from 10° C. to 20° C.; and
In step-e) the suitable temperature ranges from −10° C. to 10° C.

The twelfth aspect of the present invention provides a process for the preparation of crystalline form-I of compound of formula-1a, comprising of;
a) Providing a solution of compound of formula-1a in a suitable solvent,
b) optionally filtering the reaction mixture,
c) removing the solvent from the reaction mixture to provide crystalline form-I of compound of formula-1a.

Wherein, in step-a) the suitable solvent can be selected from hydrocarbon solvents, ether solvents, ester solvents, polar-aprotic solvents, chloro solvents, ketone solvents, nitrile solvents, alcohol solvents, polar solvents or mixtures thereof; (or) providing a solution of compound of formula-1a in a suitable solvent can be done by combining the compound of formula-1 with any of solvent is defined above and adding with a suitable hydrochloric acid source and optionally heating the reaction mixture to a suitable temperature ranges from 35° C. to 100° C.; wherein the suitable HCl source is selected from but not limited to conc.HCl, dry HCl, HCl gas, aq.HCl, methanol-HCl, ethanol-HCl, isopropyl alcohol-HCl, ethyl acetate-HCl, 1,4-dioxane-HCl.

In step-c) the suitable technique which can be used for the removal of solvent from the reaction mixture includes but not limited to evaporation optionally under reduced pressure, flash evaporation, vacuum drying, concentrating the reaction mixture, atmospheric distillation, distillation under reduced pressure, distillation by using a rotational distillation device such as a Buchi Rotavapor, agitated thin film drying (ATFD), melt extrusion, spray drying, freeze drying (lyophilization), spray-freeze drying, addition of suitable anti-solvent to the reaction mixture followed by filtration of the precipitated solid, cooling the clear solution to lower temperatures to precipitate the solid followed by filtration of the reaction mixture or by any other suitable techniques known in the art.

Preferred embodiment of the present invention provides a process for the preparation of crystalline form-I of compound of formula-1a, comprising:
a) adding aqueous hydrochloric acid to the mixture of compound of formula-1 and water,
b) distilling off the solvent from the mixture to provide crystalline form-I of compound of formula-1a.

Further preferred embodiment of the present invention provides a process for the preparation of crystalline form-I of compound of formula-1a, comprising:
a) dissolving the compound of formula-1a in water,
b) lyophilizing the solution obtained in step-a) to provide crystalline form-I of compound of formula-1a.

Apart from the key starting materials, intermediates and the above mentioned impurities, the formation of following compounds as impurities has been observed during the synthesis of compound of formula-1a by the process of the present invention.

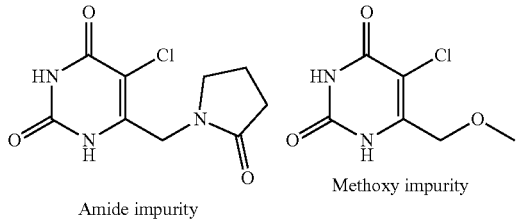

Amide impurity    Methoxy impurity

All the impurities discussed in the present invention are controlled well within the limits in the final compound of formula-1a as suggested by ICH guidelines and most of the impurities are in non-detectable levels.

An embodiment of the present invention provides compound of formula-1a substantially free of compound of formula-2a, compound of formula-3a, 5-hydro impurity, deschloro impurity, amide impurity, methoxy impurity.

The term "substantially free of" as used in the present invention means the compound of formula-1a has said impurities in a level of less than 0.15% by HPLC.

In an embodiment the term "substantially free of" means the compound of formula-1a has said impurities in a level of less than 0.1% by HPLC.

In an embodiment the term "substantially free of" means the compound of formula-1a has said impurities in a level of less than 0.05% by HPLC.

In another embodiment the term "substantially free of" means the compound of formula-1a has said impurities in a level of less than 0.001% by HPLC.

In another embodiment the term "substantially free of" means the compound of formula-1a is completely free of said impurities.

The compound of formula-1a produced by the process of the present invention is having purity of greater than 99%, preferably greater than 99.5%, more preferably greater than 99.9% by HPLC, most preferably greater than 99.95% by HPLC.

The thirteenth aspect of the present invention provides a novel crystalline polymorph of 5-chloro-6-[(2-iminopyrrolidin-1-yl)methyl]pyrimidine-2,4-(1H,3H)-dione hydrochloride compound of formula-1a. The said novel crystalline polymorph is characterized by its PXRD pattern as illustrated in FIG. 11.

Figure 11:
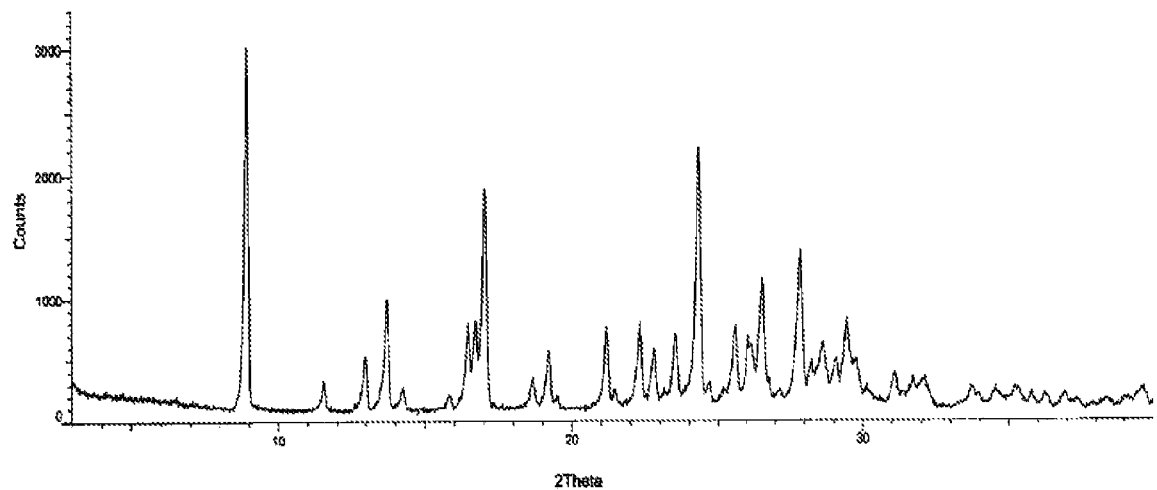
FIG. 11: Illustrates the PXRD pattern of novel crystalline polymorph of compound of formula-1a of the present invention.

The fourteenth aspect of the present invention provides a process for the preparation of novel crystalline polymorph of compound of formula-1a having PXRD pattern as shown in FIG. 11, comprising of;
a) Adding a mixture of dimethylacetamide and dimethylsulfoxide to 5-chloro-6-[(2-iminopyrrolidin-1-yl)methyl] pyrimidine-2,4-(1H,3H)-dione compound of formula-1 at a suitable temperature,
b) adding hydrochloric acid to the reaction mixture at a suitable temperature,
c) heating the reaction mixture to a suitable temperature,
d) optionally filtering the reaction mixture,
e) combining the solution with a suitable solvent at a suitable temperature,
f) filtering the solid and drying the material to provide novel crystalline polymorph of compound of formula-1a having PXRD pattern as shown in FIG. 11.

Wherein, in step-a) and step-b) the suitable temperature ranges from 0° C. to 30° C.;
In step-c) the suitable temperature ranges from 35° C. to 100° C.;
In step-e) the suitable solvent can be selected from ketone solvents and the suitable temperature ranges from −30° C. to 30° C.

The solution obtained in step-c) of the above described process may optionally be treated with charcoal or any other suitable material to remove color and/or to clarify the solution.

In step-d) of the above process, filtering the reaction mixture/solution can be carried out by passing it through paper, cloth, glass fiber or other membrane material or a bed of a clarifying agent such as Celite® or hyflow. Depending upon the equipment used and the concentration and temperature of the solution, the filtration apparatus may optionally need to be preheated to avoid premature crystallization.

The 5-chloro-6-[(2-iminopyrrolidin-1-yl)methyl]pyrimidine-2,4-(1H,3H)-dione compound of formula-1 and its hydrochloride which are utilized as input in the above described processes can be synthesized by any of the processes known in the art or according to the present invention.

Figure 14:
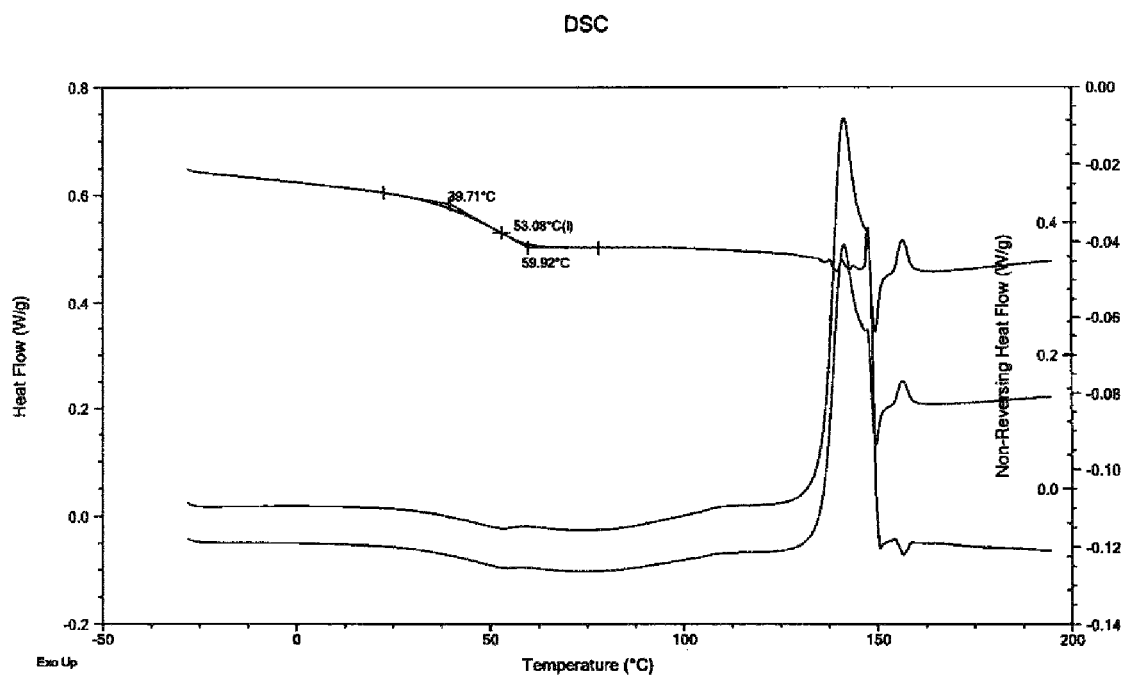
FIG. 14: Illustrates the DSC thermogram of amorphous polymorph of combination drug consisting of 2'-deoxy-5-(trifluoromethyl) uridine and 5 chloro-6-[(2-iminopyrrolidin-1-yl)methyl] pyrimidine-2,4-(1H,3H)-dione monohydrochloride.

The fifteenth aspect of the present invention provides an amorphous polymorph of the combination drug consisting of 2'-deoxy-5-(trifluoromethyl) uridine and 5-chloro-6-[(2-iminopyrrolidin-1-yl)methyl] pyrimidine-2,4-(1H,3H)-dione monohydrochloride. The said amorphous polymorph is substantially depicted in the FIG. 15 and its DSC thermogram is substantially depicted in FIG. 14.

Further aspect of the present invention provides a process for the preparation of amorphous polymorph of the combination drug consisting of 2'-deoxy-5-(trifluoromethyl) uridine and 5-chloro-6-[(2-iminopyrrolidin-1-yl)methyl] pyrimidine-2,4-(1H,3H)-dione monohydrochloride as following steps:
a) dissolving 2'-deoxy-5-(trifluoromethyl) uridine and 5-chloro-6-[(2-iminopyrrolidin-1-yl)methyl] pyrimidine-2,4-(1H,3H)-dione monohydrochloride in a suitable solvent,
b) optionally filtering the reaction mixture for particle free,
c) isolating an amorphous polymorph from the reaction mixture obtained in step-a) or step-b).

Wherein in step-a) the suitable solvent is selected from alcohol solvents, nitrile solvents, polar solvents such as water, polar aprotic solvents, ether solvents, chloro solvents, ester solvents and/or mixtures thereof; the molar ratio of 2'-deoxy-5-(trifluoromethyl) uridine and 5-chloro-6-[(2-iminopyrrolidin-1-yl)methyl] pyrimidine-2,4-(1H,3H)-dione mono-hydrochloride is used about 1:0.1 to 1:1 or 0.1:1 to 1:1.

in step-c) isolating refers to the solvent removal by known techniques which are selected from but not limited to removal by distillation, by decanting, by filtration, cooling the clear solution to lower temperatures to precipitate the solid followed by filtration of the reaction.

Preferred embodiment of the present invention provides a process for the preparation of amorphous polymorph of the combination drug consisting of 2'-deoxy-5-(trifluoromethyl) uridine and 5-chloro-6-[(2-iminopyrrolidin-1-yl)methyl] pyrimidine-2,4-(1H,3H)-dione monohydrochloride as following steps:
a) dissolving 2'-deoxy-5-(trifluoromethyl) uridine and 5-chloro-6-[(2-iminopyrrolidin-1-yl)methyl] pyrimidine-2,4-(1H,3H)-dione monohydrochloride in methanol,
b) distilling off the solvent from the mixture obtained in step-a) to provide an amorphous polymorph.

The amorphous polymorph of the combination drug consisting of 2'-deoxy-5-(trifluoromethyl) uridine and 5-chloro-6-[(2-iminopyrrolidin-1-yl)methyl] pyrimidine-2,4-(1H, 3H)-dione monohydrochloride of the present invention is useful for the preparation of various pharmaceutical formulations.

An embodiment of the present invention provides use of amorphous polymorph of the combination drug consisting of 2'-deoxy-5-(trifluoromethyl) uridine and 5-chloro-6-[(2-iminopyrrolidin-1-yl)methyl] pyrimidine-2,4-(1H,3H)-dione monohydrochloride for the preparation of various pharmaceutical formulations.

The other embodiment of the present invention provides pharmaceutical composition comprising amorphous polymorph of the combination drug consisting of 2'-deoxy-5-(trifluoromethyl) uridine and 5-chloro-6-[(2-iminopyrrolidin-1-yl)methyl] pyrimidine-2,4-(1H,3H)-dione monohydrochloride and at least one pharmaceutically acceptable excipient.

The 2'-deoxy-5-(trifluoromethyl) uridine which is utilized as input in the above described process can be synthesized by any of the processes known in the art or according to the present invention.

Further aspect of the present invention provides an improved process for the preparation thymidine, α,α,α-trifluoro-, 3',5'-bis(4-methylbenzoate) compound of formula-Ba comprising:
a) treating the compound of formula-E with trimethylsilyl chloride or trimethylsilyl bromide in presence of hexamethyldisilazane [HMDS] to provide the compound of formula-D,
b) reacting the compound of formula-D with the compound of formula-Ca in presence of Lewis acid in a suitable solvent to provide the compound of formula-Ba,
c) optionally purifying the compound of formula-Ba obtained in step-b).

Wherein in step-b) the suitable solvent is selected from alcohol solvents, nitrile solvents, polar solvents such as water, polar aprotic solvents, ether solvents, chloro solvents, ester solvents and/or mixtures thereof; the suitable Lewis acid is defined as above; the suitable temperature ranges from 15° C. to reflux of the solvent used.

Preferred embodiment of the present invention provides an improved process for the preparation thymidine, α,α,α-trifluoro-, 3',5'-bis(4-methylbenzoate) compound of formula-Ba comprising:

a) treating the compound of formula-E with trimethylsilyl chloride in presence of hexamethyldisilazane [HMDS] to provide the compound of formula-D,
b) reacting the compound of formula-D with the compound of formula-Ca in presence of Zinc chloride in dichloromethane to provide the compound of formula-Ba,
c) purifying the compound of formula-Ba obtained in step-b) from methanol.

Another aspect of the present invention provides an improved process for the preparation compound of formula-A comprising:
a) treating the compound of formula-E with trimethylsilyl chloride or trimethylsilyl bromide in presence of hexamethyldisilazane [HMDS] to provide the compound of formula-D,
b) reacting the compound of formula-D with the compound of formula-Ca in presence of Lewis acid in a suitable solvent to provide the compound of formula-Ba,
c) optionally purifying the compound of formula-Ba obtained in step-b),
d) treating the compound of formula-Ba with a suitable base in a suitable solvent to provide the compound of formula-A,
e) optionally purifying the compound of formula-A obtained in step-d).

Wherein in step-b) and step-d) the suitable solvent is selected from alcohol solvents, nitrile solvents, polar solvents such as water, polar aprotic solvents, ether solvents, chloro solvents, ester solvents and/or mixtures thereof;

in step-b) the suitable Lewis acid is defined as above;

in step-d) the suitable base is selected from inorganic bases such as alkali metal carbonates, alkali metal hydroxide, alkali metal hydrides, alkali metal amides, organic base such as triethylamine, alkali metal alkoxide or mixture thereof.

Preferred embodiment of the present invention provides an improved process for the preparation compound of formula-A comprising:
a) treating the compound of formula-E with trimethylsilyl chloride in presence of hexamethyldisilazane [HMDS] to provide the compound of formula-D,
b) reacting the compound of formula-D with the compound of formula-Ca in presence of Zinc chloride in dichloromethane to provide the compound of formula-Ba,
c) purifying the compound of formula-Ba obtained in step-b) from methanol.
d) treating the compound of formula-Ba with sodium methoxide in methanol to provide the compound of formula-A.

Further, the 2'-deoxy-5-(trifluoromethyl) uridine compound of formula-A obtained according to the present invention is designated as crystalline Form-A and its powder X-ray diffraction pattern having peaks at about 7.1, 7.3, 9.8, 10.4, 14.3, 14.7, 18.9, 20.2, 21.6, 23.2, 23.8 and 32.2±0.2° 2-theta. Its DSC thermogram having endotherm at about 190°±3° C. and shown in FIG. 13.

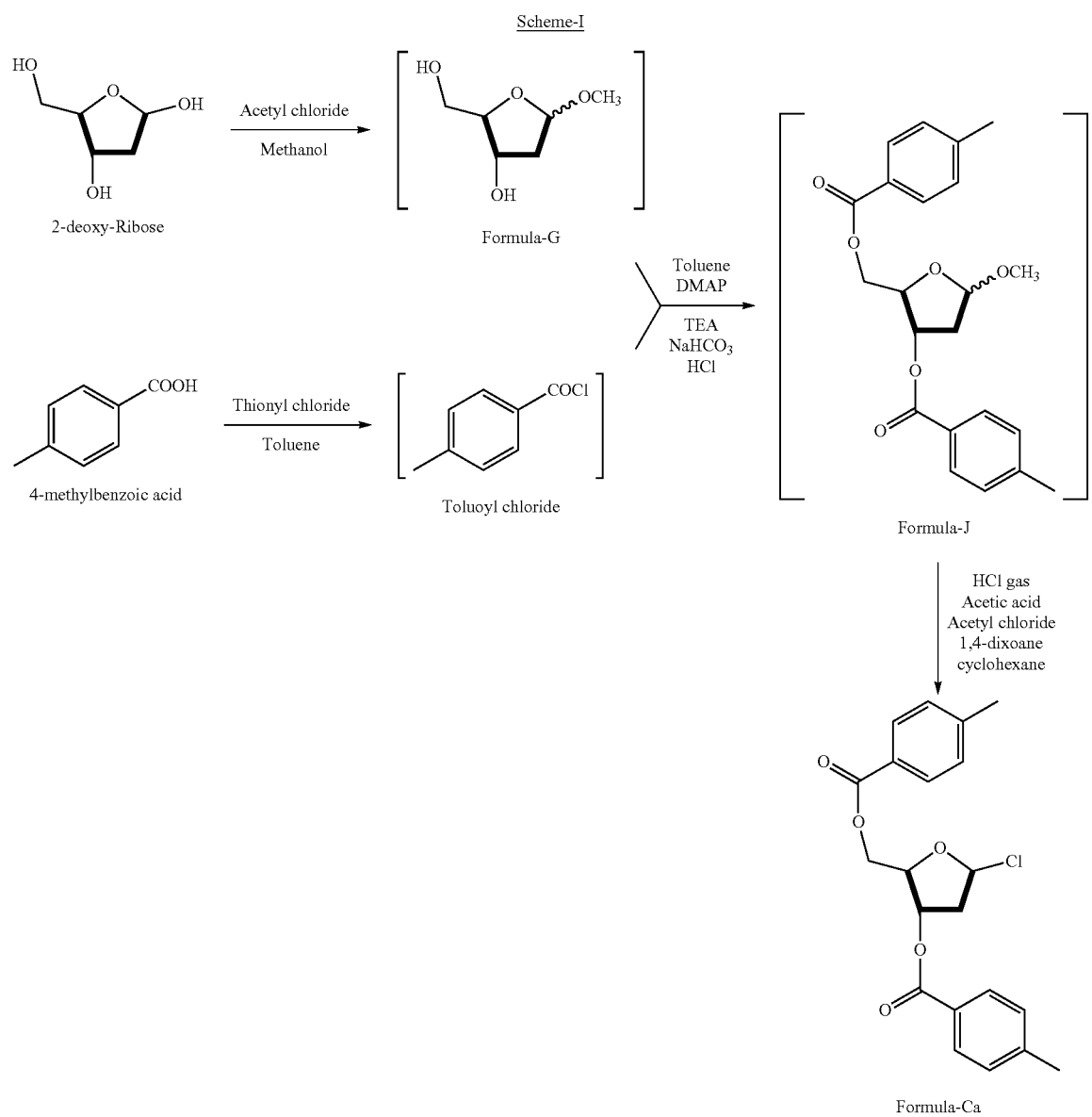
Scheme-I
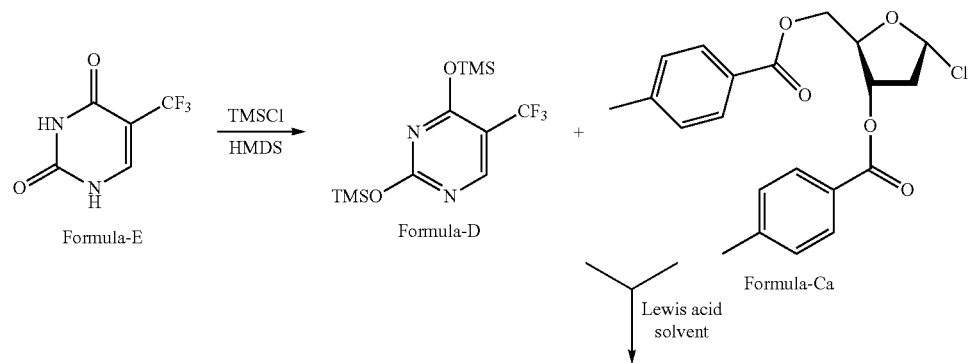
Scheme-II

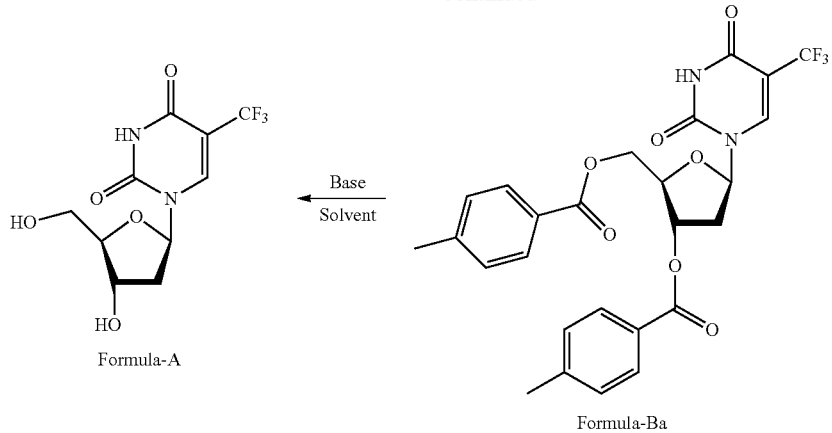

Formula-A ← Base / Solvent ← Formula-Ba

The compound of formula-1a produced by the process of the present invention is having purity of greater than 99%, preferably greater than 99.5%, more preferably greater than 99.7%, most preferably greater than 99.8% by HPLC.

HPLC Method of Analysis:

The 5-chloro-6-[(2-iminopyrrolidin-1-yl)methyl]pyrimidine-2,4-(1H,3H)-dione hydrochloride compound of formula-1a produced by the process of the present invention was analyzed by HPLC under the following conditions; Apparatus: A liquid chromatographic system equipped with variable wavelength UV detector; Column: X Bridge shield RP 18, 4.6×150 mm, 3.5µ (or) equivalent; Wavelength: 210 nm; Column temperature: 25° C.; Injection volume: 5 µL; Diluent: Acetonitrile:Water (20:80 v/v); Elution: Gradient; Buffer: Accurately transfer 1000 mL of milli-Q-water into a suitable clean and dry beaker. Transfer 1.36 gms of potassium dihydrogen phosphate and 3.0 gms of 1-octane sulfonic acid sodium salt anhydrous into 1000 mL of milli-Q-water and mix well. Filter this solution through 0.22 µm Nylon membrane filter paper; Mobile phase-A: Buffer (100%); Mobile phase-B: Acetonitrile:Buffer (70:30 v/v).

The PXRD analysis of compounds of the present invention was carried out by using BRUKER/D8 ADVANCE X-Ray diffractometer using CuKα radiation of wavelength 1.5406 A° and at a continuous scan speed of 0.03°/min.

The novel crystalline polymorphs and pure amorphous form of compound of formula-1a of the present invention can be utilized as input for the preparation of any known polymorphic form of compound of formula-1a and it can also be used in the preparation of novel polymorphic forms of compound of formula-1a.

The compound of formula-1a produced by any of the processes of the present invention can be further micronized or milled to get desired particle size to achieve desired solubility profile based on different forms of pharmaceutical composition requirements. Techniques that may be used for particle size reduction includes but not limited to single or multi-stage micronization using cutting mills, pin/cage mills, hammer mills, jet mills, fluidized bed jet mills, ball mills and roller mills. Milling or micronization may be performed before drying or after drying of the product.

The crystalline polymorphs and amorphous forms as described in the present invention can be used in the preparation of pharmaceutical composition.

The best mode of carrying out the present invention is illustrated by the below mentioned examples. These examples are provided as illustration only and hence should not be construed as limitation to the scope of the invention.

EXAMPLES

Example-1: Preparation of 5-chloro-6-(chloromethyl)pyrimidine-2,4(1H,3H)-dione (Formula-3a)

Sulfuryl chloride (302 ml) was slowly added to a pre-cooled mixture of 6-(chloromethyl)pyrimidine-2,4(1H,3H)-dione compound of formula-2a (200 gm) and acetic acid (1400 ml) at 15-20° C. under nitrogen atmosphere. Raised the temperature of the reaction mixture to 25-30° C. and stirred for 7 hrs at same temperature. Filtered the solid, washed with ethyl acetate and suck dried the material to get the title compound.
Yield: 180 gm.

Example-2: Purification of 5-chloro-6-(chloromethyl)pyrimidine-2,4(1H,3H)-dione (Formula-3a)

Figure 8:
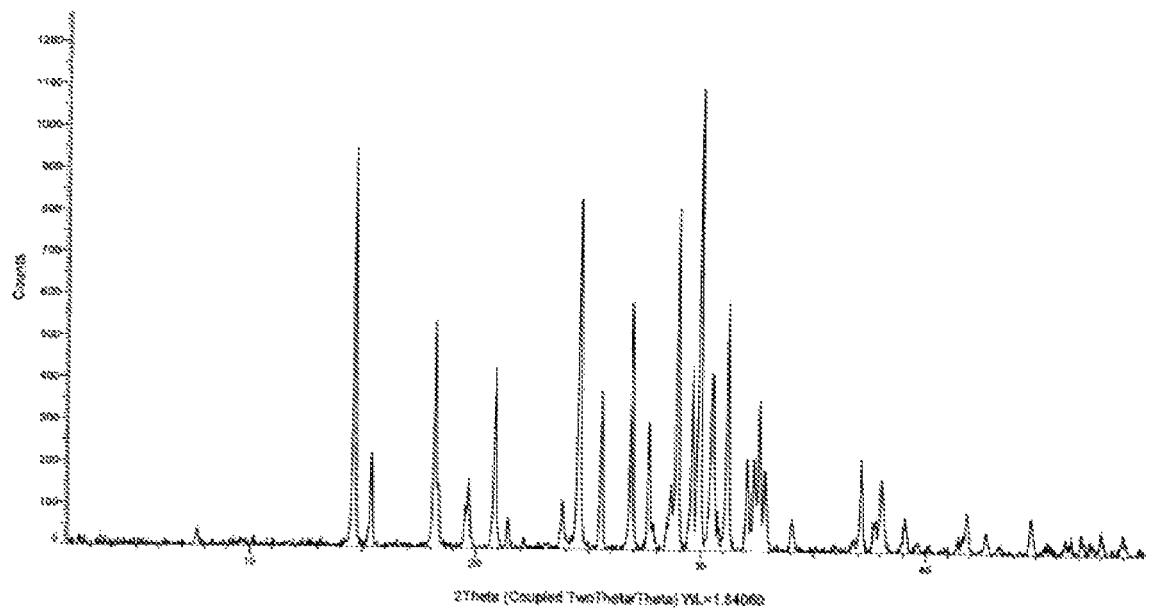
FIG. 8: Illustrates the PXRD pattern of compound of formula-3a obtained according to example-2.

Dimethylformamide (1000 ml) was added to compound of formula-3a obtained in example-1 at 25-30° C. Heated the reaction mixture to 60-65° C. and stirred for 40 min at the same temperature. Cooled the reaction mixture to 25-30° C. Filtered the reaction mixture through hyflow bed and washed the hyflow bed with dimethylformamide. Water (2000 ml) was slowly added to the filtrate at 25-30° C. Cooled the reaction mixture to 5-10° C. and stirred for 2 hrs at the same temperature. Filtered the precipitated solid, washed with water and dried the material to get the pure title compound.
The PXRD pattern of the obtained compound is shown in FIG. 8.
Yield: 160 gm; M.R.: 225-230° C.

Example-3: Preparation of 5-chloro-6-[(2-iminopyrrolidin-1-yl)methyl]pyrimidine-2,4-(1H,3H)-dione (Formula-1)

1,8-Diazabicyclo[5.4.0]undec-7-ene (203 gm) was slowly added to a pre-cooled mixture of 5-chloro-6-(chloromethyl)pyrimidine-2,4(1H,3H)-dione compound of formula-3a (100 gm), pyrrolidin-2-imine hydrochloride salt compound of formula-4a (74.2 gm) and methanol (1000 ml) at 0-5° C. Heated the reaction mixture to 65-70° C. and stirred for 8 hrs at the same temperature. Cooled the reaction mixture to 0-5°

Figure 9:
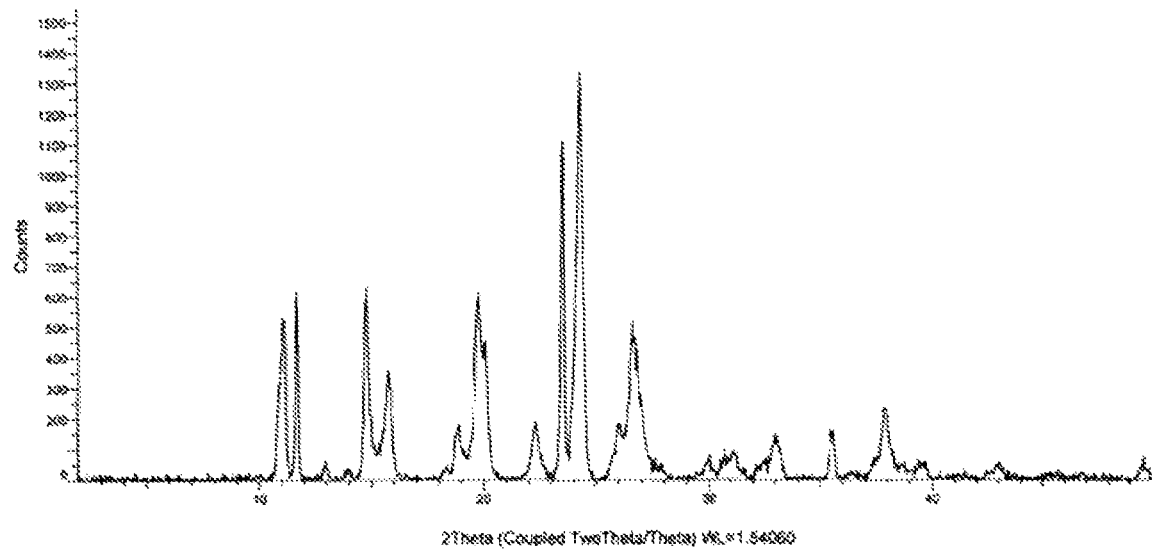
FIG. 9: Illustrates the PXRD pattern of compound of formula-1 obtained according to example-3.

C. and stirred for 2 hrs at the same temperature. Filtered the solid, washed with methanol and suck dried the material to get the title compound.
The PXRD pattern of the obtained compound is shown in FIG. 9.
Yield: 95 gm; Purity by HPLC: 97.65%.

Example-4: Purification of Compound of Formula-1

Figure 10:
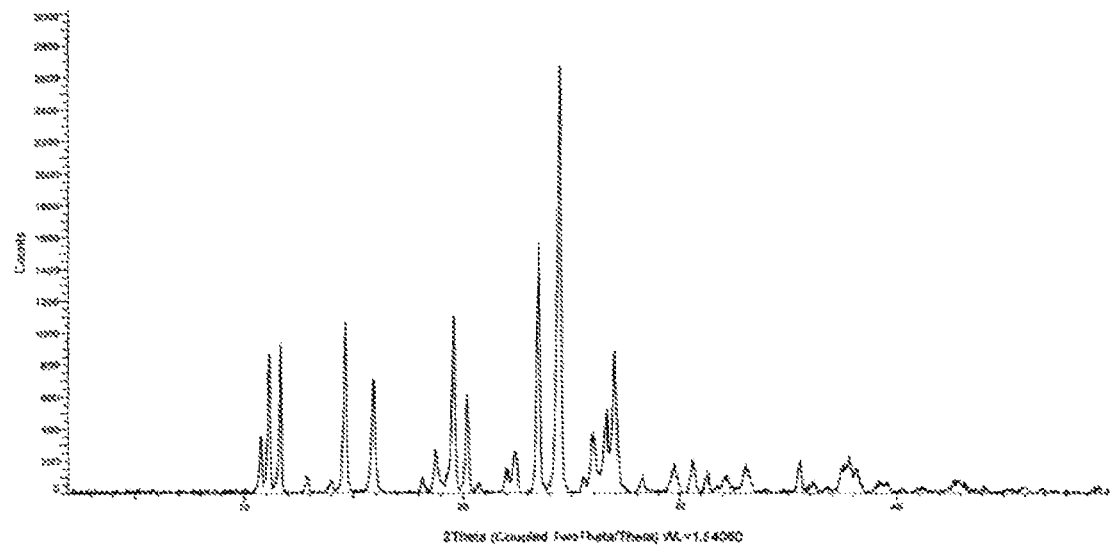
FIG. 10: Illustrates the PXRD pattern of compound of formula-1 obtained according to example-4.

Water (800 ml) and 25% aqueous hydrochloric acid solution (150 ml) were added to compound of formula-1 obtained in example-3 at 25-30° C. and stirred the reaction mixture for 15 min at the same temperature. Charcoal (8 gm) was added to the reaction mixture at 25-30° C. and stirred for 90 min at the same temperature. Filtered the reaction mixture through hyflow bed and washed the hyflow bed with water. Ethyl acetate (300 ml) was added to the obtained filtrate at 25-30° C. and stirred the reaction mixture for 15 min at the same temperature. Settled the reaction mixture for 15 min. Both the organic and aqueous layers were separated and extracted the aqueous layer with ethyl acetate. Combined the aqueous layers, basified the reaction mixture with triethylamine (60 ml) at 25-30° C. and stirred for 90 min at the same temperature. Filtered the precipitated solid and washed with water. Water (800 ml) and aqueous hydrochloric acid solution (150 ml) were added to the obtained compound at 25-30° C. and stirred the reaction mixture for 30 min at the same temperature. Filtered the reaction mixture through hyflow bed and washed the hyflow bed with water. Ethyl acetate (300 ml) was added to the filtrate at 25-30° C. and stirred the reaction mixture for 15 min at the same temperature. Both the organic and aqueous layers were separated and extracted the aqueous layer with ethyl acetate. Combined the aqueous layers, slowly basified the reaction mixture with triethylamine (60 ml) at 25-30° C. and stirred for 2 hrs at the same temperature. Filtered the precipitated solid, washed with water and dried the material to get the pure title compound.
The PXRD pattern of the obtained compound is shown in FIG. 10.
Yield: 70 gm; M.R.: 245-250° C. (decomposition); Purity by HPLC: 99.7%.

Example-5: Preparation of Crystalline Form-I of Compound of Formula-1a

25% Aqueous hydrochloric acid solution (7.5 ml) was slowly added to a mixture of 5-chloro-6-[(2-iminopyrrolidin-1-yl)methyl]pyrimidine-2,4-(1H,3H)-dione compound of formula-1 (5 gm) and water (50 ml) at 25-30° C. and stirred the reaction mixture for 15 min at the same temperature. Filtered the reaction mixture through hyflow bed and washed the hyflow bed with water. Conc.hydrochloric acid (20 ml) was added to the filtrate at 25-30° C. and stirred the reaction mixture for 3 hrs at the same temperature. Cooled the reaction mixture to 0-5° C. and stirred for 3 hrs at same temperature. Filtered the precipitated solid, washed with isopropyl alcohol and dried the material to get the title compound.
The PXRD pattern of the obtained compound is similar to the PXRD pattern of crystalline form-I described in U.S. Pat. No. 9,527,833B2.
Yield: 4 gm.

Example-6: Preparation of Crystalline Form-I of Compound of Formula-1a

25% Aqueous hydrochloric acid solution (7.5 ml) was slowly added to a mixture of compound of formula-1 (5 gm) and water (50 ml) at 25-30° C. and stirred the reaction mixture for 15 min at the same temperature. Filtered the reaction mixture through hyflow bed and washed the hyflow bed with water. Distilled off water completely from the filtrate under reduced pressure and dried the obtained material to get the title compound.
Yield: 5 gm.

Example-7: Preparation of Crystalline Form-I of Compound of Formula-1a

A mixture of compound of formula-1a (5 gm) and water (50 ml) was stirred for 15 min at 25-30° C. Filtered the reaction mixture through hyflow bed and washed the hyflow bed with water. Distilled off water completely from the filtrate under reduced pressure and dried the obtained material to get the title compound. Yield: 4.5 gm.

Example-8: Preparation of Crystalline Form-I of Compound of Formula-1a

25% Aqueous hydrochloric acid solution (7.5 ml) was slowly added to a mixture of compound of formula-1 (5 gm) and water (50 ml) at 25-30° C. and stirred the reaction mixture for 15 min at the same temperature. Filtered the reaction mixture through hyflow bed and washed the hyflow bed with water. The filtrate was subjected to lyophilization and the obtained material was dried to get the title compound.
Yield: 5 gm.

Example-9: Preparation of Crystalline Form-I of Compound of Formula-1a

A mixture of compound of formula-1a (5 gm) and water (50 ml) was stirred for 15 min at 25-30° C. Filtered the reaction mixture through hyflow bed and washed the hyflow bed with water. The filtrate was subjected to lyophilization and the obtained material was dried to get the title compound. Yield: 4.5 gm.

Example-10: Preparation of Crystalline Form-II of Compound of Formula-1a

25% Aqueous hydrochloric acid solution (108 ml) was slowly added to a mixture of 5-chloro-6-[(2-iminopyrrolidin-1-yl)methyl]pyrimidine-2,4-(1H,3H)-dione compound of formula-1 (72 gm) and water (576 ml) at 25-30° C. and stirred the reaction mixture for 15 min at the same temperature. Filtered the reaction mixture through hyflow bed and washed the hyflow bed with water. Cooled the filtrate to 15-20° C., conc.hydrochloric acid (36 ml) was slowly added to it and stirred the reaction mixture for 1 hr at the same temperature. Further cooled the reaction mixture to 0-5° C., conc.hydrochloric acid (252 ml) was added to it and stirred for 90 min at same temperature. Filtered the precipitated solid, washed with isopropyl alcohol and dried the material to get the title compound.
The PXRD pattern of the obtained compound is similar to the PXRD pattern of crystalline form-II described in U.S. Pat. No. 9,527,833B2.
Yield: 59 gm; Purity by HPLC: 99.96%.

Example-11: Preparation of Crystalline Form-II of Compound of Formula-1a

A mixture of compound of formula-1a (0.5 gm) and tetrahydrofuran (50 ml) was heated to 70-75° C. Water (10 ml) was added to the reaction mixture and stirred the reaction mixture for 5 min at the same temperature. Cooled the reaction mixture to 0-5° C. and stirred the reaction mixture for 30 min at the same temperature. Filtered the precipitated solid and suck dried the material to get the title compound.
Yield: 0.31 gm.

Example-12: Preparation of Crystalline Form-II of Compound of Formula-1a

A mixture of compound of formula-1 (5 gm) and methyl ethyl ketone (100 ml) was heated to 65-70° C. Water (50 ml) was added to the reaction mixture and stirred the reaction mixture for 30 min at the same temperature. 1:1 Mixture of water and hydrochloric acid (10 ml) was added to the reaction mixture at 65-70° C. and stirred the reaction mixture for 2 hrs at the same temperature. Cooled the reaction mixture to 0-5° C., methyl tert.butyl ether (100 ml) was added and stirred the reaction mixture for 10 min at the same temperature. Acetone (150 ml) was added to the reaction mixture at 0-5° C. and stirred the reaction mixture for 15 min at the same temperature. Filtered the precipitated solid and dried the material to get the title compound. Yield: 4.0 gm.

Example-13: Preparation of Crystalline Form-III of Compound of Formula-1a

A mixture of compound of formula-1 (5 gm) and methanolic HCl (25 ml) was heated to 60-65° C. and stirred the reaction mixture for 1 hr at the same temperature. Cooled the reaction mixture to 25-30° C. and stirred for 1 hr at the same temperature. Filtered the solid, washed with methanol and dried the material to get the title compound.
The PXRD pattern of the obtained compound is similar to the PXRD pattern of crystalline form-III described in U.S. Pat. No. 9,527,833B2.
Yield: 5 gm.

Example-14: Preparation of Novel Crystalline Polymorph of Compound of Formula-1a A mixture of compound of formula-1a (23 gm) and dimethyl sulfoxide (460 ml) was slowly heated to 70-75° C. and stirred the reaction mixture for 15 min at the same temperature. Filtered the reaction mixture to make it particle free. The obtained filtrate was added to isobutyl acetate (1.38 Lt) at 25-30° C. and stirred the reaction mixture for 20 min at the same temperature. Filtered the precipitated solid and dried the material to get the title compound.
The PXRD pattern of the obtained compound is shown in FIG. 1.
Yield: 19.5 gm.

Example-15: Alternate Process for the Preparation of Novel Crystalline Polymorph of Compound of Formula-1a A mixture of compound of formula-1a (0.5 gm) and dimethyl acetamide (30 ml) was heated to 75-80° C. and stirred for 20 min at the same temperature. Dimethyl sulfoxide (20 ml) was added to the reaction mixture at 75-80° C. and stirred the reaction mixture for 15 min at the same temperature. Acetone (60 ml) was added to the reaction mixture at 75-80° C. and stirred for 20 min at the same temperature. Filtered the precipitated solid and dried the material to get the title compound.
The PXRD pattern of the obtained compound is similar to FIG. 1.
Yield: 0.39 gm.

Example-16: Alternate Process for the Preparation of Novel Crystalline Polymorph of Compound of Formula-1a A 3:1 mixture of dimethylsulfoxide and isopropyl alcohol (40 ml) was added to compound of formula-1a (0.5 gm) at 25-30° C. Heated the reaction mixture to 75-80° C. and stirred the reaction mixture for 15 min at the same temperature. The obtained solution was added to isobutyl acetate (80 ml) at 25-30° C. and stirred the reaction mixture for 15 min at the same temperature. Filtered the precipitated solid and dried the material to get the title compound. The PXRD pattern of the obtained compound is similar to FIG. 1.
Yield: 0.4 gm.

Example-17: Preparation of Pure Amorphous Form of Compound of Formula-1a

A 3:1 mixture of acetone and water (160 ml) was added to compound of formula-1a (4 gm) at 25-30° C. Slowly heated the reaction mixture to 60-65° C. and stirred for 15 min at the same temperature. Filtered the reaction mixture to make it particle free. The obtained filtrate was spray dried to get the title compound.
The PXRD pattern of the obtained compound is shown in FIG. 2.
Yield: 1.2 gm.

Example-18: Preparation of Amorphous Solid Dispersion Comprising Compound of Formula-1a and PVP K-30

Figure 3:
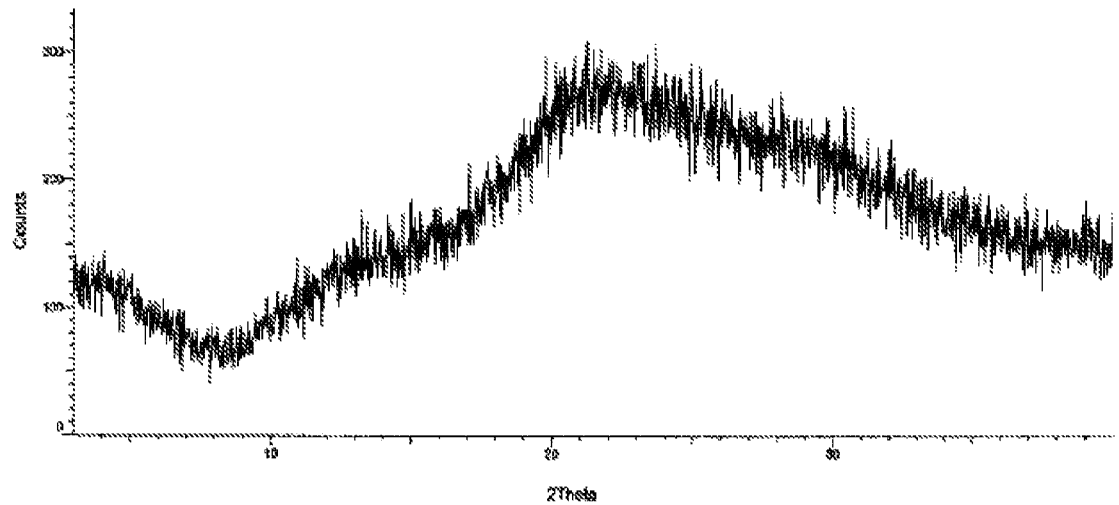
FIG. 3: Illustrates the PXRD pattern of amorphous solid dispersion comprising compound of formula-1a and PVP K-30.

Acetone (30 ml) and water (10 ml) were added to a mixture of compound of formula-1a (0.5 gm) and PVP K-30 (0.5 gm) at 25-30° C. Slowly heated the reaction mixture to 55-60° C. and stirred for 15 min at the same temperature. Filtered the reaction mixture to make it particle free. Charged the obtained filtrate into Buchi flask, distilled off the solvent completely from the filtrate under reduced pressure and dried the material to get the title compound. The PXRD pattern of the obtained compound is shown in FIG. 3.
Yield: 0.82 gm.

Figure 4:
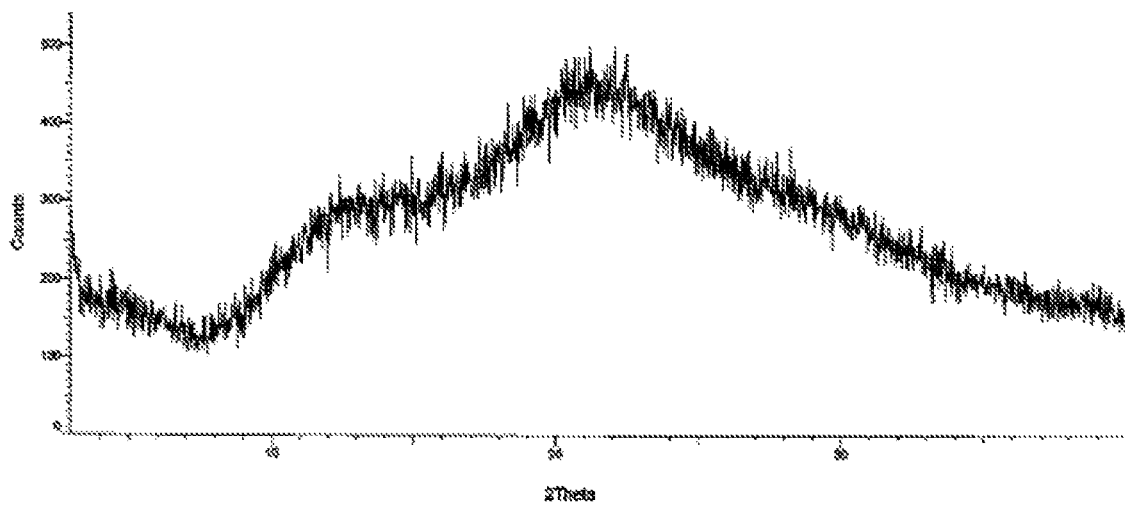
FIG. 4: Illustrates the PXRD pattern of amorphous solid dispersion comprising compound of formula-1a and HPC.

Example-19: Preparation of Amorphous Solid Dispersion Comprising Compound of Formula-1a and HPC Acetone (30 ml) and water (10 ml) were added to a mixture of compound of formula-1a (0.5 gm) and HPC (0.5 gm) at 25-30° C. Slowly heated the reaction mixture to 45-50° C. and stirred for 15 min at the same temperature. Charged the obtained solution into Buchi flask, distilled off the solvent completely under reduced pressure and dried the obtained solid to get the title compound. The PXRD pattern of the obtained compound is shown in FIG. 4.
Yield: 0.85 gm.

Figure 5:
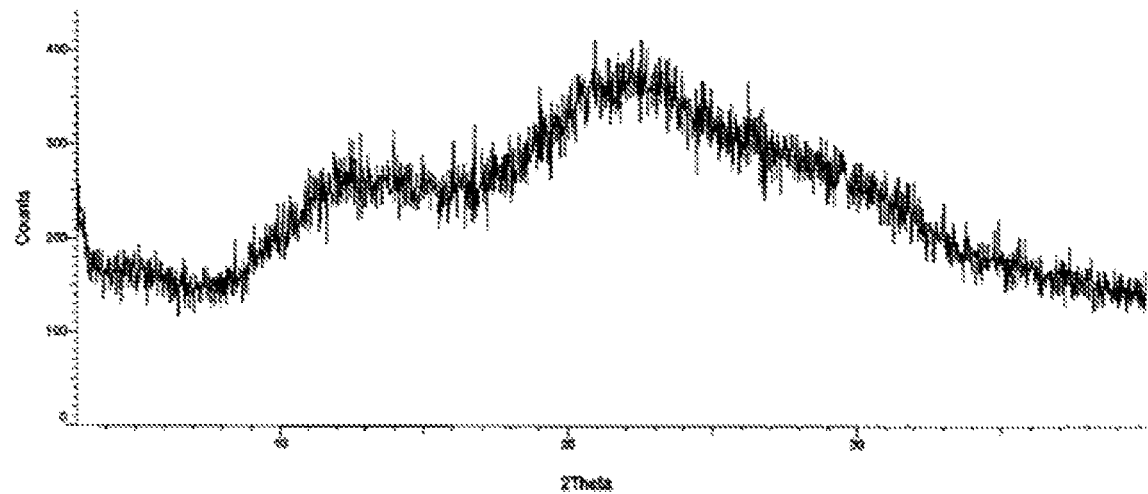
FIG. 5: Illustrates the PXRD pattern of amorphous solid dispersion comprising compound of formula-1a and HPMC.

Example-20: Preparation of Amorphous Solid Dispersion Comprising Compound of Formula-1a and HPMC Acetone (30 ml) and water (10 ml) were added to a mixture of compound of formula-1a (0.5 gm) and HPMC (0.5 gm) at 25-30° C. Slowly heated the reaction mixture to 45-50° C. and stirred for 10 min at the same temperature. Charged the obtained solution into Buchi flask, distilled off the solvent completely under reduced pressure and dried the obtained solid to get the title compound. The PXRD pattern of the obtained compound is shown in FIG. 5.
Yield: 0.92 gm.

Example-21: Preparation of Novel Crystalline Polymorph of 5-chloro-6-[(2-imino pyrrolidin-1-yl)methyl]pyrimidine-2,4-(1H,3H)-dione Hydrochloride (Formula-1a)

A 1:1 mixture of dimethylacetamide and dimethylsulfoxide (200 ml) was added to 5-chloro-6-[(2-iminopyrrolidin-1-yl)methyl]pyrimidine-2,4-(1H,3H)-dione compound of formula-1 (5 gm) at 25-30° C. Hydrochloric acid (5 ml) was added to the reaction mixture at 25-30° C. Heated the reaction mixture to 75-80° C. and filtered the solution to make it particle free. The obtained filtrate was added to pre-cooled acetone (400 ml) at 0-5° C. and stirred the reaction mixture for 3 hr at the same temperature. Filtered the precipitated solid under reduced pressure and suck dried the material to get the title compound.
The PXRD pattern of the obtained compound is shown in FIG. 11.
Yield: 5.1 gm.

Example-22: Preparation of 6-(chloromethyl)pyrimidine-2,4(1H,3H)-dione

A mixture of ethyl 4-chloro-3-oxobutanoate (100 gm), polyphosphoric acid (400 gm) and urea (109.4 gm) was heated to 90-95° C. and stirred the reaction mixture for 3 hr at the same temperature. Further heated the reaction mixture to 120-125° C. and stirred for 10 hr at the same temperature. Reduced the temperature of the reaction mixture to 90-95° C. and chilled water was slowly added to it at the same temperature. Cooled the reaction mixture to 0-5° C. and stirred for 3 hr at the same temperature. Filtered the solid and washed with chilled water. Methanol (500 ml) and water (500 ml) were added to the obtained compound at 25-30° C. Heated the reaction mixture to 70-75° C. and stirred for 40 min at the same temperature. Charcoal (8 gm) was added to the reaction mixture at 70-75° C. and stirred for 40 min at the same temperature. Filtered the reaction mixture through hyflow bed and washed the hyflow bed with methanol. Cooled the filtrate to 0-5° C. and stirred for 3 hr at the same temperature. Filtered the precipitated solid, washed with chilled water and dried the material to get the title compound.
Yield: 23.0 gm; M.R.: 253-255° C.

Example-23: Preparation of Crystalline 5-chloro-6-[(2-iminopyrrolidin-1-yl)methyl]pyrimidine-2,4-(1H,3H)-dione Hydrochloride Dimethyl Sulfoxide Solvate Aqueous hydrochloride solution (102 ml) was added to a mixture of compound of formula-1 (200 gm) and dimethyl sulfoxide (3.2 Lt) at room temperature. Slowly heated the reaction mixture to 45-50° C. and stirred the reaction mixture for 30 min at the same temperature. Filtered the reaction mixture through highflow bed. The obtained filtrate was added to isobutyl acetate (6.0 Lt) at 20-25° C. and stirred the reaction mixture for 60 minutes at the same temperature. Filtered the material, washed with isobutyl acetate (200 ml) and dried to get the title compound. Purity by HPLC: 99.87%. The PXRD pattern of the obtained compound is shown in FIG. 6; DMSO content: 20.99% w/w. DSC thermogram is shown in FIG. 7. Yield: 252.0 gm.

Example-24: Preparation of Thymidine, α,α,α-trifluoro-, 3',5'-bis(4-methylbenzoate) [or] (2R,3S,5R)-5-(2,4-dioxo-5-(trifluoromethyl)-3,4-dihydropyrimidin-1(2H)-yl)-2-(((4-methylbenzoyl)oxy)methyl)tetrahydrofuran-3-yl 4-methylbenzoate Compound of Formula-Ba Step-a):
A mixture of methanol (1200 ml) and acetyl chloride (4.22 ml) was stirred for 30 minutes at 5-10°. To this reaction mixture 2-deoxy-D-ribose (100 g) was added at 5-10° C. and stirred for 5 hours at the same temperature. To this reaction mixture sodium bicarbonate was added at 5-10° C. and stirred for 20 minutes at the same temperature. The reaction mixture was filtered on hyflow bed and washed with methanol. Distilled off the solvent completely under reduced pressure and co-distilled with toluene to get (2R,3S)-2-(hydroxymethyl)-5-methoxytetrahydrofuran-3-ol compound of formula-G an oily residue.

Step-b):
Thionyl chloride (342.8 g) was added to the mixture of para toluic acid (274 g) and toluene (274 ml) at 25-30° C. The reaction mixture was heated to 75-80° C. and stirred for 5 hours at the same temperature. Further heated the reaction mixture to 110-115° C. and distilled off the solvent under nitrogen pressure at the same temperature and co-distilled with toluene to get para toluoyl chloride.

Step-c):
Toluene (1320 ml), dimethylaminopyridine (21.82 g), triethylamine (311.1 ml) were added to (2R,3S)-2-(hydroxymethyl)-5-methoxytetrahydrofuran-3-ol compound of formula-G obtained in step-a) at 25-30° C. Slowly added the para toluoyl chloride obtained in step-b) to the reaction mixture at 25-30° C. and stirred the reaction mixture for 2 hours at the same temperature. Water was added to the reaction mixture at 25-30° C. and stirred for 15 minutes at same temperature. Separated both the organic and aqueous layers and the aqueous layer was extracted with toluene. Combined the organic layers and washed with aqueous hydrochloric acid solution, water, aqueous sodium bicarbonate solution and followed by water. Distilled off the solvent under the reduced pressure to get the (2R,3S)-5-methoxy-2-(((4-methylbenzoyl)oxy)methyl) tetrahydrofuran-3-yl 4-methylbenzoate compound of formula-J.

Step-d):
1,4-dioxane (537 ml) was added to the mixture of acetic acid (1047 ml) and chloroform (537 ml) at 25-30° C. and the reaction mixture to 10-15° C. Acetyl chloride (16.35 ml) was added to the reaction mixture at 10-15° C. and stirred for 15 minutes at the same temperature. Hydrochloric acid gas (120 g) was passed into this reaction mixture at 10-15° C. (2R,3S)-5-methoxy-2-(((4-methylbenzoyl)oxy)methyl)tetrahydrofuran-3-yl 4-methyl benzoate compound of formula-J obtained in step-c) was added to the reaction mixture at 10-15° C. and stirred for 3 hours at the same temperature. Filtered the precipitated solid and washed with cyclohexane. To this compound cyclohexane (600 ml) was added at 10-15° C. and stirred for 30 minutes at the same temperature. Filtered the solid and washed with cyclohexane to get the (2R,3S,5R)-5-chloro-2-(((4-methylbenzoyl)oxy)methyl)tetrahydrofuran-3-yl 4-methyl benzoate compound of formula-Ca.

Step-e):

A mixture of trifluoro methyl uracil (139 g), hexamethyldisilazane (374.4 g) and trimethyl silyl chloride (4.21 g) was heated to 120-125° C. and stirred for 3 hours at the same temperature. Cooled the reaction mixture to 55-60° C. and distilled off the reaction mixture under reduced pressure. To this reaction mixture dichloromethane (1050 ml), zinc chloride (5.28 g) and followed by (2R,3S,5R)-5-chloro-2-(((4-methylbenzoyl)oxy)methyl) tetrahydrofuran-3-yl 4-methyl benzoate compound of formula-Ca obtained in step-d) were added at 25-30° C. and stirred the reaction mixture for 3 hours at the same temperature. Cooled the reaction mixture to 10-15° C. and slowly added the aqueous sodium bicarbonate solution. Raised the temperature of the reaction mixture to 25-30° C. and stirred for 30 minutes at the same temperature. Filtered the reaction mixture through the hyflow bed and washed with dichloromethane. Separated the both organic and aqueous layer and the aqueous layer was extracted with dichloromethane. Combined the organic layers and washed with water. Distilled off the solvent completely from the organic layer under reduced pressure and co-distilled with methanol. Methanol (600 ml) was added to the obtained compound at 25-30° C. Heated the reaction mixture to 40-45° C. and stirred for 40 minutes at the same temperature. Filtered the solid, washed with methanol and dried to get the title compound.
Yield: 175 g, purity by HPLC: 98.66%, undesired isomer: 98.66%.

Example-25: Preparation of
2'-deoxy-5-(trifluoromethyl) uridine Compound of
Formula-A Thymidine, α,α,α-trifluoro-, 3',5'-bis(4-methylbenzoate) compound of formula-Ba (10 g) was added to the pre-cooled mixture of sodium methoxide (7.24 ml) and methanol (50 ml) at 10-15° C. and stirred for 60 minutes at the same temperature. Neutralized the reaction mixture using methanolic hydrochloric acid and filtered reaction mixture. Distilled off the solvent completely from the filtrate under reduced pressure and co-distilled with toluene. Filtered the solid and washed with toluene. Acetone (30 ml) was added to the obtained compound and stirred for 10 minutes. Filtered the reaction mixture and washed with acetone. Distilled off the solvent completely from the filtrate. Dissolved the obtained compound in acetone (35 ml) at 25-30° C. and filtered the reaction mixture. To this reaction mixture dichloromethane (160 ml) was added at 25-30° C. and stirred for 3 hours at the same temperature. Filtered the precipitated solid, washed with dichloromethane and dried to get the title compound.
Yield: 4.6 g. Purity by HPLC: 99.39%, undesired isomer: 0.18% by HPLC.

Example-26: Preparation of
2'-deoxy-5-(trifluoromethyl) uridine

Thymidine, α,α,α-trifluoro-, 3',5'-bis(4-methylbenzoate) (100 g) was added to the pre-cooled mixture of sodium methoxide (72.43 ml) and methanol (500 ml) at 10-15° C. and stirred for 90 minutes at the same temperature. Cooled the reaction mixture to 0-5° C. and neutralized the reaction mixture using Methanolic HCl. Raised the temperature of the reaction mixture to 25-30° C. and filtered reaction mixture. Distilled off the solvent completely from the filtrate under reduced pressure and co-distilled with toluene. Toluene (300 ml) was added to the obtained compound at 25-30° C. and stirred for 20 minutes. Filtered the solid and washed with toluene. Acetone (300 ml) was added to the obtained compound and stirred for 20 minutes. Filtered the mixture and washed with acetone. Distilled off the solvent completely from the filtrate and co-distilled with methanol. Methanol (150 ml) was added to the obtained compound at 25-30° C. and heated to the mixture to 65-70° C. for 15 minutes. Cooled the mixture to 55-60° C. and toluene (800 ml) was added to it. Further cooling the mixture to 25-30° C. and stirred for 3 hours at the same temperature. Filtered the precipitated solid, washed with toluene and dried to get the title compound.
Yield: 39 gms.

Figure 12:
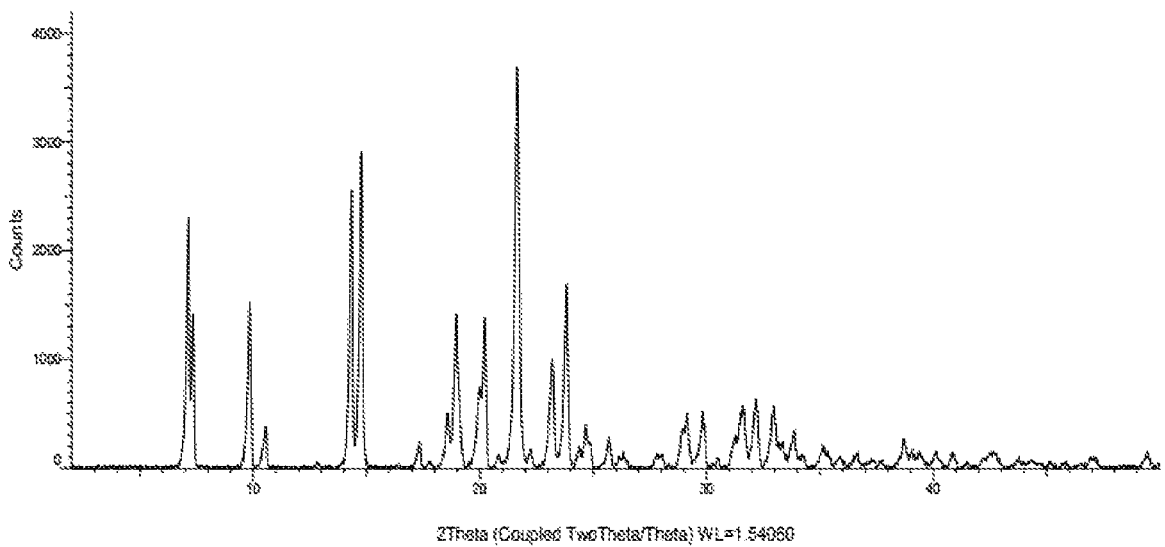
FIG. 12: Illustrates the PXRD pattern of compound of formula-A obtained according to example-27.
Figure 13:
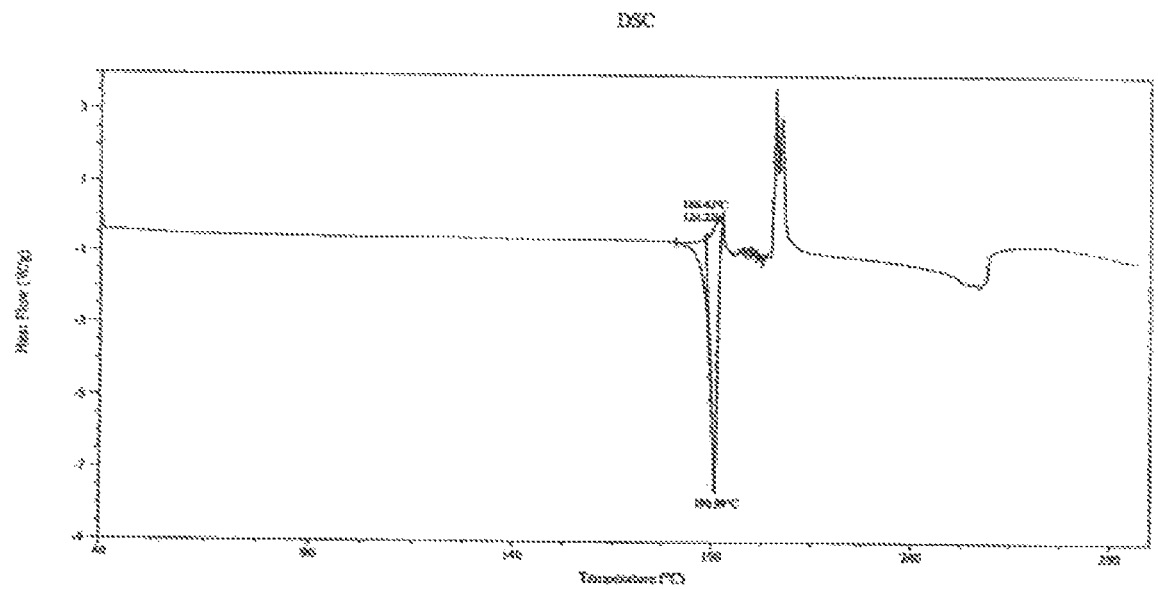
FIG. 13: Illustrates the DSC thermogram of compound of formula-A obtained according to example-27.

Example-27: Purification of
2'-deoxy-5-(trifluoromethyl) uridine Compound of
Formula-A Dissolved 2'-deoxy-5-(trifluoromethyl) uridine (16 g) in methanol (40 ml) at 65-70° C., the reaction mixture was slowly cooled to −10 to −5° C. and stirred for 3 hours at the same temperature. Filtered the precipitated solid, washed with methanol and dried to get the title compound.
Yield: 10 g. Purity by HPLC: 99.72%, undesired isomer: not detected. PXRD and DSC of the obtained compound are shown in FIG. 12 and FIG. 13 respectively.

Example-28: Preparation of Amorphous Polymorph
of the Combination Drug Consisting of 2'-deoxy-5-
(trifluoromethyl) uridine and 5-chloro-6-[(2-imino-
pyrrolidin-1-yl) methyl]pyrimidine-2,4-(1H,3H)-
dione Monohydrochloride (1:0.5)

Figure 15:
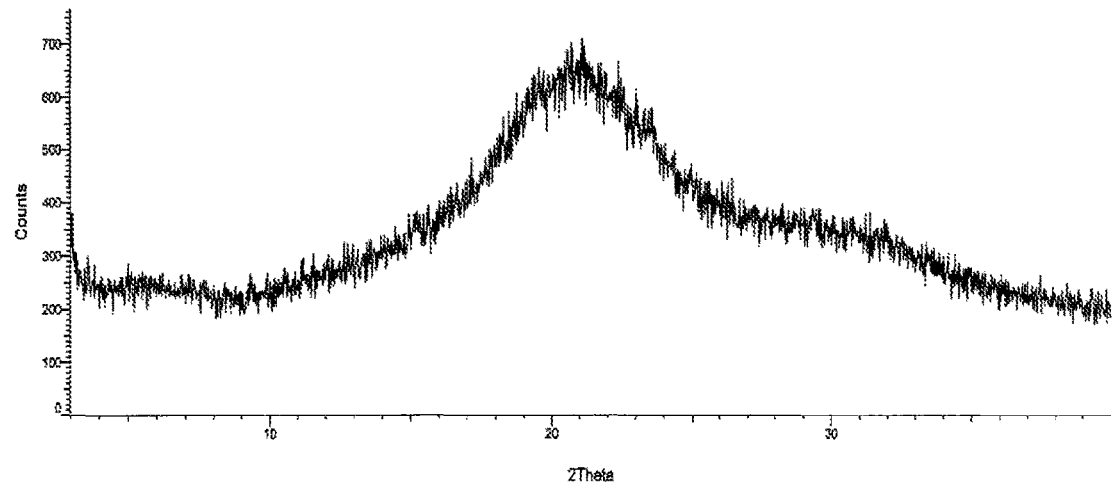
FIG. 15: Illustrates the PXRD pattern of amorphous polymorph of combination drug consisting of 2'-deoxy-5-(trifluoromethyl) uridine and 5 chloro-6-[(2-iminopyrrolidin-1-yl)methyl] pyrimidine-2,4-(1H,3H)-dione monohydrochloride.
Figure 16:
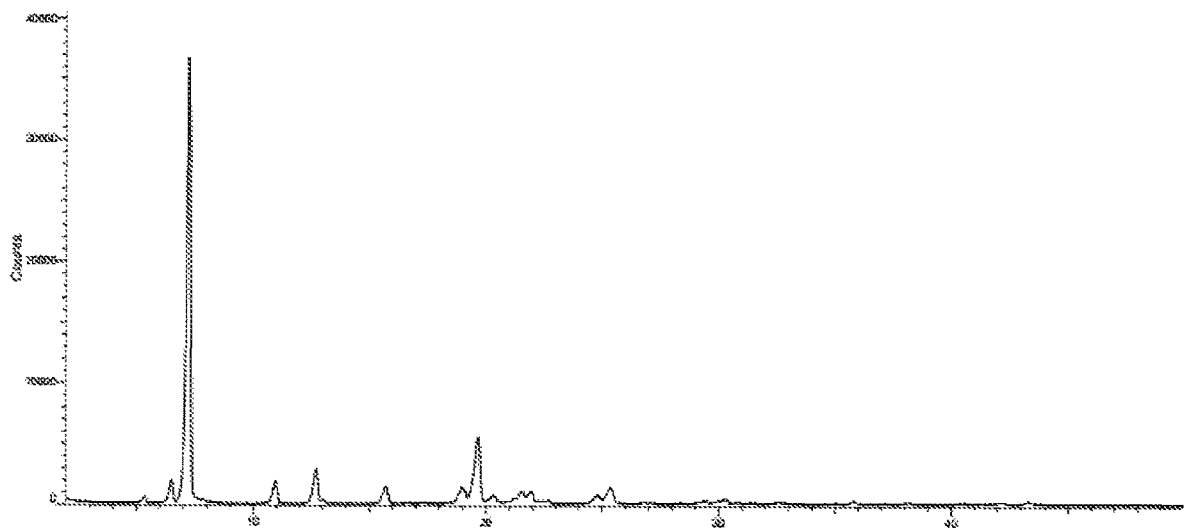
FIG. 16: Illustrates the PXRD pattern of compound of formula-Ba obtained according to example-24.
Figure 17:
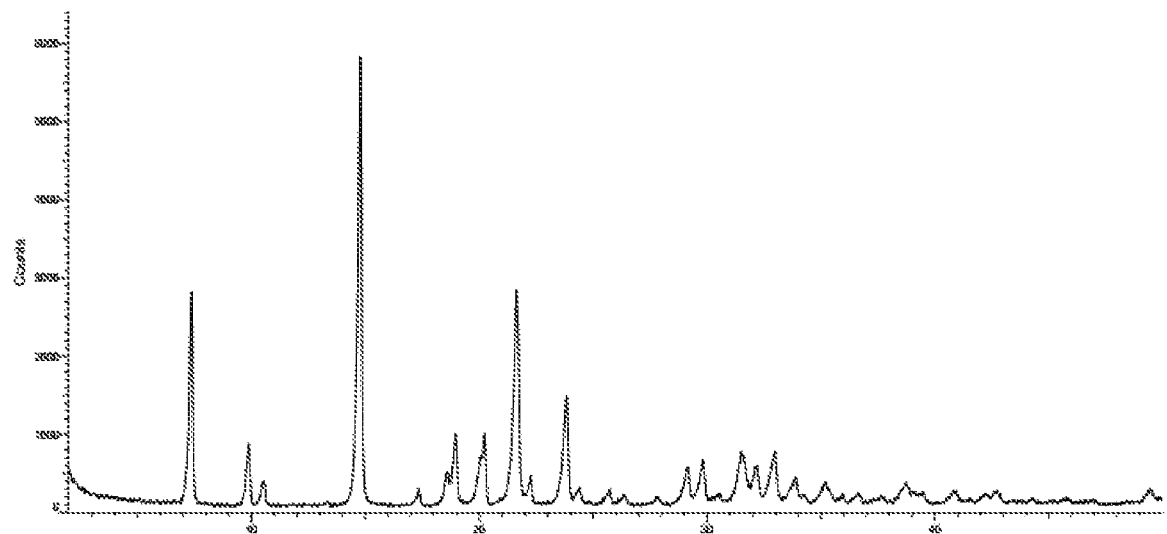
FIG. 17: Illustrates the PXRD pattern of compound of formula-A obtained according to example-26.

Dissolved the 2'-deoxy-5-(trifluoromethyl) uridine (5 g) and 5-chloro-6-[(2-iminopyrrolidin-1-yl)methyl]pyrimidine-2,4-(1H,3H)-dione monohydrochloride (2.5 g) in methanol (375 ml) at 25-30° C. Filtered the reaction mixture for particle free and distilled off solvent completely from the filtrate under reduced pressure to get the title compound.
Yield: 6.8 g. PXRD of the obtained compound is shown in FIG. 15.

Example-29: Preparation of Amorphous Polymorph
of the Combination Drug Consisting of 2'-deoxy-5-
(trifluoromethyl) uridine and 5-chloro-6-[(2-imino-
pyrrolidin-1-yl) methyl]pyrimidine-2,4-(1H,3H)-
dione Monohydrochloride (1.5:1)

Dissolved the 2'-deoxy-5-(trifluoromethyl) uridine (750 mg) and 5-chloro-6-[(2-iminopyrrolidin-1-yl)methyl]pyrimidine-2,4-(1H,3H)-dione monohydrochloride (500 mg) in methanol (100 ml) at 60-65° C. Filtered the reaction mixture for particle free and distilled off the solvent completely from the filtrate under reduced pressure to get the title compound.
Yield: 1.1 g. PXRD of the obtained compound is similar to the FIG. 15.

Example-30: Preparation of Amorphous Polymorph
of the Combination Drug Consisting of 2'-deoxy-5-
(trifluoromethyl) uridine and 5-chloro-6-[(2-imino-
pyrrolidin-1-yl)methyl]pyrimidine-2,4-(1H,3H)-
dione Monohydrochloride (1.75:1)

Dissolved the 2'-deoxy-5-(trifluoromethyl) uridine (875 mg) and 5-chloro-6-[(2-iminopyrrolidin-1-yl)methyl]pyrimidine-2,4-(1H,3H)-dione monohydrochloride (500 mg) in methanol (100 ml) at 60-65° C. Filtered the reaction mixture for particle free and distilled off solvent completely from the filtrate under reduced pressure to get the title compound.
Yield: 1.2 g. PXRD of the obtained compound is similar to the FIG. 15.

Comparative Example-1: Preparation of Thymidine, α,α,α-trifluoro-, 3',5'-bis(4-chlorobenzoate) [or] ((2R,3S,5R)-3-((4-chlorobenzoyl)oxy)-5-(2,4-dioxo-5-(trifluoromethyl)-3,4-dihydropyrimidin-1(2H)-yl)tetrahydrofuran-2-yl)methyl 4-Chlorobenzoate Compound of Formula-Bb A mixture of trifluoro methyl uracil (41.9 g), hexamethyldisilazane (113.10 g) and trimethyl silyl chloride (1.26 g) was heated to 134-140° C. and stirred for 3 hours at the same temperature. Cooled the reaction mixture to 55-60° C. and distilled off the hexamethyldisilazane and un-reacted trimethyl silyl chloride under vacuum. To this reaction mixture dichloromethane (350 ml), zinc chloride (1.58 g) and (2R, 5R)-5-chloro-2-(((4-chlorobenzoyl)oxy)methyl)tetrahydrofuran-3-yl 4-chlorobenzoate (50 g) was added at 25-30° C. and stirred for 3 hours at the same temperature. Cooled the reaction mixture to 10-15° C. and slowly added the aqueous sodium bicarbonate solution. Raised the reaction mixture temperature to 25-30° C. and stirred for 30 minutes at the same temperature. Filtered the reaction mixture through hyflow bed and washed with dichloromethane. Separated the both organic and aqueous layer and the aqueous layer was extracted with dichloromethane. Combined the organic layers and washed with water and distilled off the solvent completely under vacuum. Co-distilled with ethanol and cooled the reaction mixture to 25-30° C. Ethanol (200 ml) was added to the reaction mixture. Heated the reaction mixture to 40-45° C. and stirred for 40 minutes at the same temperature. Filtered the precipitated solid, washed with methanol and dried to get the title compound.
Yield: 65 g. Purity by HPLC: 78.06%, undesired isomer: 19.93%.

Comparative Example-2: Preparation of 2'-deoxy-5-(trifluoromethyl) uridine or Compound of Formula-A The mixture of thymidine, α,α,α-trifluoro-, 3',5'-bis(4-chlorobenzoate) compound of formula-Bb (60 g) and methanol (300 ml) was cooled to 0-5° C. and stirred for 10 minutes at the same temperature. To this reaction sodium methoxide (58.5 ml) was slowly added at 0-5° C. and stirred for 40 minutes at the same temperature. Neutralized the reaction mixture using methanolic hydrochloric acid and filtered reaction mixture and stirred for 40 minutes at 25-30° C. Distilled off the solvent completely from the filtrate under reduced pressure and co-distilled with acetone. Acetone (180 ml) was added to the obtained residue and stirred for 30 minutes. Filtered the reaction mixture and washed with acetone. Distilled off the solvent completely from the filtrate, n-heptane was added to the obtained residue and decanted the solvent. Ethyl acetate was added to it and stirred for 2 hours at 25-30° C. Filtered the solid, washed with ethyl acetate and dried to get the title compound.
Yield: 19.2 g, M.R: 177-179° C., purity by HPLC: 78.86%, undesired isomer: 12.44%.

Comparative Example-3: Purification of 2'-deoxy-5-(trifluoromethyl) uridine

The mixture of 2'-deoxy-5-(trifluoromethyl) uridine (9.2 g) and ethyl acetate (184 ml) was heated to 75-80° C., filtered reaction mixture and washed with ethyl acetate. Distilled off solvent completely from the reaction mixture. Ethyl acetate (38.8 ml) was added to this reaction mixture and stirred for 2 hours. Filtered the solid, washed with ethyl acetate and dried to get the title compound.
Yield: 3.89 g, purity by HPLC: 93.23%, undesired isomer: 3.15%.

We claim:
1. Crystalline 5-chloro-6-[(2-iminopyrrolidin-1-yl)methyl]pyrimidine-2,4-(1H, 3H)-dione hydrochloride dimethyl sulfoxide solvate

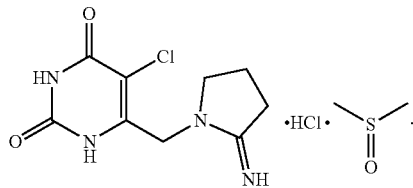

2. Crystalline 5-chloro-6-[(2-iminopyrrolidin-1-yl)methyl]pyrimidine-2,4-(1H, 3 H)-dione hydrochloride dimethyl sulfoxide solvate according to claim 1, characterized by one or more of the following:
    (i) a powder X-ray diffraction pattern comprising 2θ values at 7.9°, 15.9° and 16.9°±0.2° of 2θ,
    (ii) a powder X-ray diffraction (PXRD) pattern substantially in accordance with the pattern shown in FIG. 1 or FIG. 6; and
    (iii) its DSC thermogram as illustrated in figure-7.
3. Crystalline 5-chloro-6-[(2-iminopyrrolidin-1-yl)methyl]pyrimidine-2,4-(1H, 3 H)-dione hydrochloride dimethyl sulfoxide solvate according to claim 2, which is further characterized by its XRPD pattern having peaks at about 11.5°, 14.4°, 17.0°, 23.2°, 23.9°, 25.8° and 26.4°±0.2° of 2θ.
4. The crystalline dimethyl sulfoxide solvate according to claim 1, having dimethyl sulfoxide content in the range of about 18 to about 25% w/w.
5. A process for the preparation of crystalline 5-chloro-6-[(2-iminopyrrolidin-1-yl)methyl] pyrimidine-2,4-(1H, 3H)-dione hydrochloride dimethyl sulfoxide solvate according to claim 1, comprising:
    a) combining a hydrochloric acid source with a mixture of 5-chloro-6-[(2-iminopyrrolidin-1-yl) methyl]pyrimidine-2,4-(1H,3H)-dione and dimethylsulfoxide optionally in mixture with a first solvent,
    b) optionally heating the mixture obtained in step-a) to 35° C.-60° C.,
    c) combining the solution obtained in step-a) or step-b) with a second solvent to provide crystalline 5-chloro-6-[(2-iminopyrrolidin-1-yl)methyl]pyrimidine-2,4-(1H,3H)-dione hydrochloride dimethyl sulfoxide solvate.
6. The process according to claim 5, wherein,
    the first solvent in step-a) is selected from polar solvents such as water, polar-aprotic solvents, alcohol solvents, ether solvents or mixtures thereof;
    the hydrochloric acid source in step-a) is selected from aqueous/dilute HCl, conc.HCl, dry HCl, HCl gas, aq.HCl, methanol-HCl, ethanol-HCl, isopropyl alcohol-HCl, ethyl acetate-HCl and 1,4-dioxane-HCl;
    the second solvent in step-b) is selected from ketone solvents, ester solvents, hydrocarbon solvents, chloro solvents, nitrile solvents or mixtures thereof; and the temperature ranges from −20° C. to 100° C.; preferably 0° C. to 30° C.

7. A process for the preparation of crystalline dimethyl sulfoxide solvate of 5-chloro-6-[(2-iminopyrrolidin-1-yl) methyl]pyrimidine-2,4-(1H,3H)-dione hydrochloride according to claim 1, comprising:
   a) providing a solution of 5-chloro-6-[(2-iminopyrrolidin-1-yl)methyl]pyrimidine-2,4-(1H,3H)-dione hydrochloride in dimethyl sulfoxide,
   b) combining the solution with a second solvent at a suitable temperature to provide crystalline dimethyl sulfoxide solvate of 5-chloro-6-[(2-iminopyrrolidin-1-yl)methyl]pyrimidine-2,4-(1H,3H)-dione hydrochloride.

8. The process according to claim 7, wherein in step-a) providing the solution can be done by combining 5-chloro-6-[(2-iminopyrrolidin-1-yl)methyl]pyrimidine-2,4-(1H, 3H)-dione compound of formula-1 with dimethylsulfoxide optionally in mixture with a first solvent, adding a suitable hydrochloric acid source and optionally heating the reaction mixture to a suitable temperature ranges from 35° C. to 100° C.

9. The process according to claim 8, wherein the first solvent is selected from polar solvents such as water, polar-aprotic solvents, alcohol solvents, ether solvents or mixtures thereof; the hydrochloric acid source is selected from aqueous/dilute HCl, conc.HCl, dry HCl, HCl gas, aq.HCl, methanol-HCl, ethanol-HCl, isopropyl alcohol-HCl, ethyl acetate-HCl and 1,4-dioxane-HCl.

10. The process according to claim 7, wherein in step-b) the second solvent is selected from ketone solvents, ester solvents, hydrocarbon solvents, chloro solvents, nitrile solvents or mixtures thereof; and the temperature ranges from −20° C. to 100° C.; preferably 0° C. to 30° C.

11. The process according to claim 7, wherein in step-a) providing the solution can be done by combining 5-chloro-6-[(2-iminopyrrolidin-1-yl)methyl]pyrimidine-2,4-(1H, 3H)-dione hydrochloride with dimethylsulfoxide optionally in mixture with a first solvent and optionally heating the reaction mixture to a suitable temperature ranges from 35° C. to 150° C.

12. The process according to claim 11, wherein the first solvent is selected from polar solvents such as water, polar-aprotic solvents, alcohol solvents, ether solvents or mixtures thereof.

13. A pharmaceutical composition comprising crystalline 5-chloro-6-[(2-iminopyrrolidin-1-yl)methyl]pyrimidine-2, 4-(1H,3H)-dione hydrochloride dimethyl sulfoxide solvate according to claim 1 and at least one pharmaceutically acceptable excipient.

* * * * *